(12) United States Patent
Kim et al.

(10) Patent No.: US 7,732,589 B2
(45) Date of Patent: Jun. 8, 2010

(54) PRIMERS FOR AMPLIFYING HSP 65 GENE OF MYCOBACTERIAL SPECIES, HSP 65 GENE FRAGMENTS AND METHOD OF IDENTIFYING MYCOBACTERIAL SPECIES WITH THE SAME

(75) Inventors: Bum-Joon Kim, Jeju-do (KR); Yoon-Ho Kook, Seoul (KR); Jeong-Mi Kim, Seoul (KR)

(73) Assignees: Seoulin Bio Science Co., Ltd., Seoul (KR); Seoul National University Industry Foundation, Seoul (KR)

( * ) Notice: Subject to any disclaimer, the term of this patent is extended or adjusted under 35 U.S.C. 154(b) by 1265 days.

(21) Appl. No.: 10/500,586

(22) PCT Filed: Jan. 21, 2003

(86) PCT No.: PCT/KR03/00131

§ 371 (c)(1),
(2), (4) Date: Sep. 9, 2004

(87) PCT Pub. No.: WO03/062470

PCT Pub. Date: Jul. 31, 2003

(65) Prior Publication Data

US 2005/0014157 A1    Jan. 20, 2005

(30) Foreign Application Priority Data

Jan. 24, 2002  (KR) ............... 10-2002-0004297
Mar. 5, 2002   (KR) ............... 10-2002-0011648

(51) Int. Cl.
C07H 21/04    (2006.01)
C07H 19/00    (2006.01)
C07H 21/02    (2006.01)

(52) U.S. Cl. ............... 536/24.33; 536/22.1; 536/23.1; 536/23.7; 536/24.1; 536/24.3; 536/24.32; 435/4; 435/6

(58) Field of Classification Search ............... 536/22.1, 536/23.1, 23.7, 24.1, 24.3, 24.32, 24.33; 435/4, 6

See application file for complete search history.

*Primary Examiner*—Rodney P. Swartz
(74) *Attorney, Agent, or Firm*—Alston & Bird LLP

(57) ABSTRACT

The present invention relates to a pair of primers specific to mycobacterial species, a polynucleotide of an hsp 65 gene fragment, and a method for the identification of mycobacterial species by using the same. More specifically, the 604-bp hsp 65 gene fragment can be applied to identification methods of *mycobacteria* such as the comparative sequence analysis method, the probe hybridization method, and PCR-RFLP, which can resolve the problems of a conventional identification method based on bio-chemical characteristics, where the genus *mycobacterium* covers various species and has a low growth rate, and of the problems of 16s rDNA. Thus, according to the identification method of the present invention, the mycobacterial species can be identified simply, economically, and accurately.

13 Claims, 8 Drawing Sheets

PRIMERS FOR AMPLIFYING HSP 65 GENE OF MYCOBACTERIAL SPECIES, HSP 65 GENE FRAGMENTS AND METHOD OF IDENTIFYING MYCOBACTERIAL SPECIES WITH THE SAME

CROSS REFERENCE TO RELATED APPLICATION

The present application is a National Phase entry of PCT/KR03/00131, filed of Jan. 21, 2003, which claims priority from Korean patent application No. 2002-004297, filed on Jan. 24, 2002, and Korean patent application No. 2002-0011648 filed on Mar. 5, 2002.

BACKGROUND OF THE INVENTION (a) Field of the Invention

The present invention relates to a pair of primers specific to mycobacterial species, more specifically to a pair of primers that can specifically amplify the hsp 65 gene of *mycobacteria*, a gene fragment of hsp 65, and an identifying method of mycobacterial species.

(b) Description of the Related Art

The genus *Mycobacterium* covers a wide range of organisms including obligate species causing serious human and animal disease such as tuberculosis, bovine tuberculosis, and leprosy; opportunistic pathogens; and saprothytic species found in the natural environment. At present, it is known that about 72 species of the genus *Mycobacterium* have been reported, of which about 25 species are involved in the human diseases.

Tuberculosis is the largest of the mycobacterial infections. The mycobacterial species causing tuberculosis include *M. tuberculosis, M. bovis, M. africanum,* and *M. microti,* which are classified as *M. tuberculosis* complex (TB complex). *M. tuberculosis* is common and important in causing tuberculosis. Tuberculosis infection decreased because of continuous use of antituberculosis drugs until the end of the 1980s, but in line with the rapid increase of AIDS and *Mycobacterium tuberculosis* with drug resistance, tuberculosis increased in developed countries in the 1990s. In particular, it has been reported that the death rate due to tuberculosis is the highest among infectious diseases in Korea, claiming about three hundred or more lives per year, because of the increase in the number of street people in the International Monetary Fund era in Korea.

*Mycobacteria* other than *Mycobacterium tuberculosis* (MOTT, or nontuberculous *mycobacteria*, NTM) causes infection in aged people and immuno-compromised patients, and its clinical manifestation is similar to tuberculosis. The occurrence of MOTT is still lower than tuberculosis in Korea, but it is quite common. It is difficult to determine the pathogenicity from isolate that is separated from a clinical sample. In addition, resistance of MOTT to most anti-tuberculosis drugs and its recurrence rate makes it difficult to treat MOTT infection. It has been reported that MOTT also cause disease in patients who are not immuno-compromised, and that 50% of mycobacterial infection in the United States is tuberculosis and 50% is MOTT infection over the past 10 years. With the spread of HIV (Human immunodeficiency virus) infection since the 1980s, MOTT has caused systemic disseminated infection of immuno-compromised patients. Thus, MOTT has been closely watched.

Mycobacterial species have different patterns of resistance to antituberculosis drugs from each other, and thus they are treated by different methods with different drugs (Wolinsky E: Mycobacterial diseases other than tuberculosis. *Clin Infect Dis* 15: 1-10, 1992). Accordingly, *mycobacteria* need to be differentiated and identified on a species level.

A biochemical method for identifying mycobacterial species is laborious and time-consuming due to the slow growing rate of *mycobacteria*. A cell wall lipid analyzing method using High-performance Lipid Chromatography (HPLC) and Thin Layer Lipid Chromatography (TLC) is difficult to perform and is costly, and thus it is carried out on a small laboratory scale. The use of conventional identifying methods has a disadvantage in that it takes a great deal of time to perform due to the slow growing rate of the *mycobacteria* (about 2-3 months for slow-growing *mycobacteria*). Thus, the treatment of mycobacterial infection can be delayed (Nolte F S, Metchock B: *Mycobacterium*, In Murray P R, Baron E J, Pfaller M A, Tenover F C, Yolken R H (eds.), Manual of clinical microbiology. American Society for Microbiology, Washington, D.C. 400-437, 1995.).

16s rDNA is commonly used as a chronometer molecule for identification of the mycobacterial species with a molecular biological method. In 1990, the nucleic acid sequence of 16s rDNA was analyzed, and it shows the phylogenetic relationship of *mycobacteria* well. Until now, various methods of identifying mycobacterial species by using the 16S rDNA have been developed and studied (Comparative sequence analysis, Probe hybridization, and Polymerization chain reaction-restriction fragment length polymorphism).

Identifying methods of mycobacterial species by using dnaJ and 23S rDNA as alternative chronometers were developed in 1994. However, dnaJ and 23S rDNA have problems in phylogenetic relationship determination and conservation of nucleic acid sequences, and thus the methods were not used for target genes (Victor T C, Jordaan A M, Van Schalkwyk E J, Coetzee G J, Van Helden P D. Strain-specific variation in the dnaJ gene of *mycobacteria*. J Med Microbiol. 44(5):332-339, 1996). In 1993, Telenti A et al. reported that a method for the identification of *mycobacteria* at the species level was developed by using polymerase chain reaction (PCR)-Restriction Enzyme Length Polymorphism of a gene fragment of hsp 65. The method involves steps of amplifying an hsp 65 gene fragment by PCR and restriction enzyme analysis of PCR products of hsp 65 with two restriction enzymes, BstEII and HaeIII, and 29 species and subspecies were differentiated by PCR-restriction enzyme pattern analysis. (Telenti A, Marchesi F, Balz M, Bally F, Bottger E C, Bodmer T. "Rapid identification of *mycobacteria* to the species level by polymerase chain reaction and restriction enzyme analysis," J. Clin. Microbiol. 31(2):175-8. 1993).

However, the above methods for identifying *mycobacteria* are disadvantageous in that the procedure involves various restriction enzymes and is expensive. In addition, the gene fragment must be differentiated to a 10 bp fragment due to the small size of the restriction enzyme fragment in the case of Hae III. Also, mycobacterial species must be identified accurately on the basis of a known restriction fragment database of each species, or they must be analyzed by comparing the electrophoresis patterns of the subject strain and its reference strain.

SUMMARY OF THE INVENTION

To resolve the above problems, an object of the present invention is to provide a pair of primers for amplifying the hsp65 gene of *mycobacteria*.

Another object of the present invention is to provide a polynucleotide of the hsp65 gene fragment that is amplified with the primers.

It is yet another object of the present invention to provide a probe or a probe set for detecting or identifying mycobacterial species comprising at least a gene fragment of the hsp 65 gene of reference mycobacterial species.

It is a still another object of the present invention to provide a simple and accurate method for the detection or identification of mycobacterial species.

It is a further object of the present invention to provide a method for the identification of mycobacterial species comprising the steps of:
(1) amplifying an hsp 65 gene fragment of *mycobacteria* of interest with primers for specifically amplifying the hsp 65 gene of *mycobacteria*;
(2) analyzing the nucleotide sequence of the amplified hsp 65 gene fragment; and
(3) comparing the nucleotide sequence of the amplified hsp 65 gene fragment obtained in step (2) with a 604-bp hsp 65 gene fragment of a reference mycobacterial species.

It is a further object to provide a method for the detection or identification of mycobacterial species comprising the steps of:
(1) amplifying an hsp 65 gene fragment of *mycobacteria* of interest with primers for specifically amplifying the hsp 65 gene of *mycobacteria*; and
(2) hybridizing the amplified hsp 65 gene fragment with a probe set comprising at least a probe of the hsp 65 gene fragment.

It is a further object to provide a method for the identification of mycobacterial species comprising the steps of amplifying an hsp 65 gene fragment of *mycobacteria* of interest with a pair of primers for specifically amplifying the hsp 65 gene of *mycobacteria*, and analyzing according to the Restriction Fragment Length Polymorphism (RFLP) analysis using the restriction enzyme recognition site in the amplified hsp 65 gene fragment.

It is a further object to provide a kit useful for the diagnosis or identification of mycobacterial species comprising a pair of primers for amplifying the hsp 65 gene of *mycobacteria*, and a restriction enzyme recognizing the restriction enzyme recognition site which is located in the amplified hsp 65 gene fragment.

It is a further object to provide a kit useful for the diagnosis or identification of mycobacterial species comprising an amplifying means comprising a pair of primers for specifically amplifying the 604-bp hsp 65 gene fragment of *mycobacteria*, a hybridization means comprising a probe set including at least a 604-bp hsp 65 gene fragment, and a labeling means for detecting the hybridized product.

BRIEF DESCRIPTION OF THE DRAWINGS

The above and the other objects and features of the present invention will become apparent from the following description given in conjunction with the accompanying drawings, in which.

DETAILED DESCRIPTION AND THE PREFERRED EMBODIMENTS

The present invention relates to a pair of primers specific to *mycobacteria*, and more specifically to a pair of primers specifically amplifying an hsp 65 gene fragment of *mycobacteria*, an hsp 65 gene fragment, and a method for the identification of *mycobacteria* with the same.

Considering the problems in conventional identification methods and the taxonomy of *mycobacteria*, the inventors provide PCR primers that can amplify *M. tuberculosis* and non-tuberculosis *mycobacteria*, an hsp 65 gene fragment as a chronometer molecule which exists in all *mycobacteria*, and a method for the identification of *mycobacteria* by using the primers and hsp 65 gene fragments. By using the restriction fragment of the amplified product of hsp 65 genes with treatment of Xho I, it is possible to differentiate *M. tuberculosis* and non-tuberculosis *mycobacteria*, and to differentiate non-tuberculosis *mycobacteria*.

Figure 1:
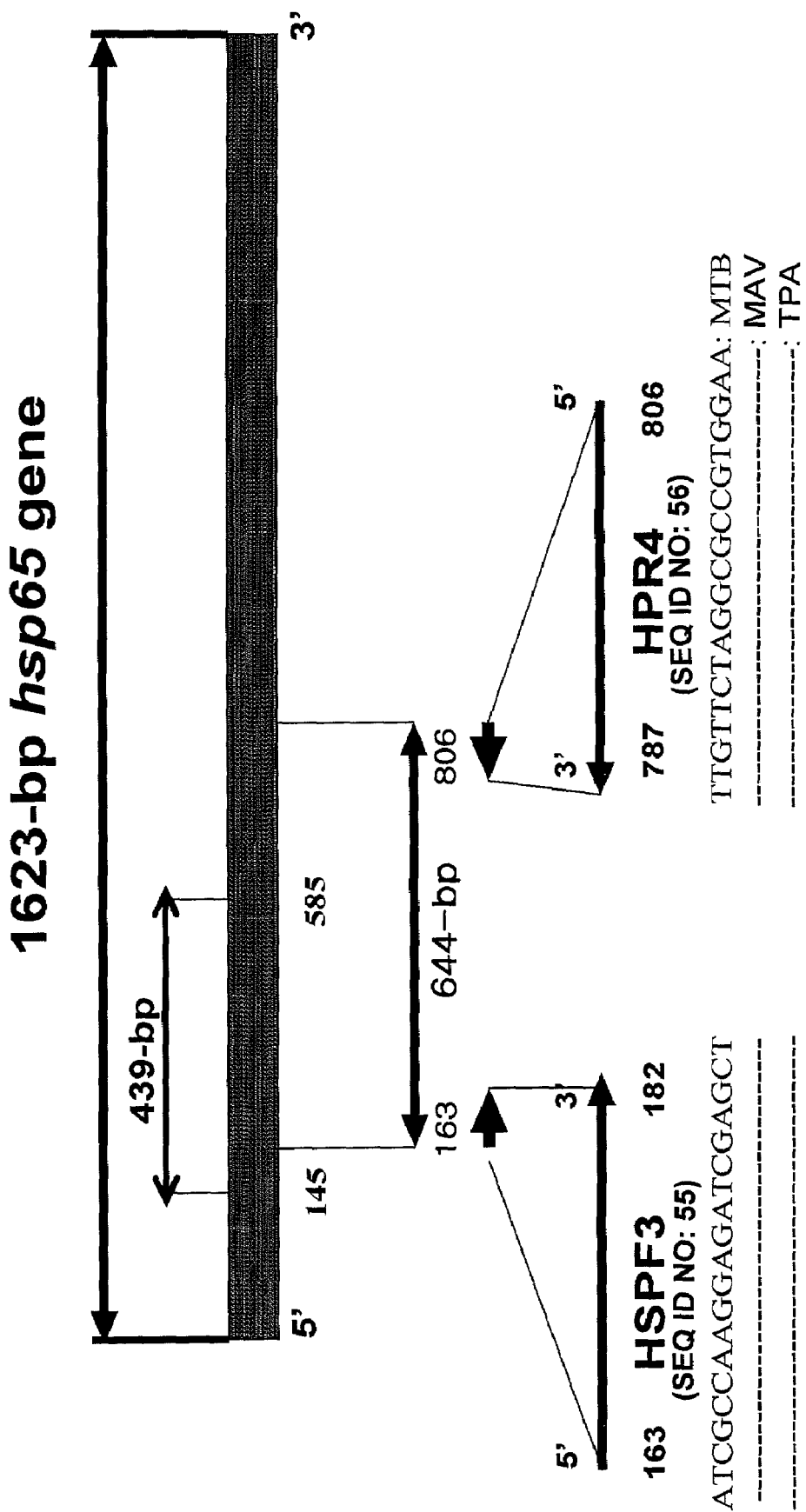
FIG. 1 shows the hsp 65 gene fragment and the primers of the present invention, namely SEQ ID NO. 55 and SEQ ID NO. 56.

In order to obtain a pair of primers that preferably amplify the hsp 65 gene of *mycobacteria*, the inventors prepared the primers on the basis of the hsp 65 gene of *M. tuberculosis* (GenBank No. M15467), *M. avium* (GenBank No. AF281650) of which 1623-bp full sequences of the hsp 65 gene were analyzed, and *T. paurometabola* (GenBank No. AF352578) which is phylogenetically closer to *mycobacteria*. The forward primer comprises 20 nucleotides located at the 163rd position to the 182nd position of the hsp 65 gene sequence of the three *mycobacteria*, and the backward primer comprises 20 nucleotides located at the 787th position to the 806th position. In addition, the modified primers or polynucleotides comprising the primers can be used for amplifying 644-bp hsp 65 gene fragments of *mycobacteria*. The primer region of the hsp 65 gene is adopted from the region of *M. tuberculosis* and *M. avium* which belong to genus *mycobacteria* and *Tsukamurella paurometabola*. Preferably, the forward primer is 5'-ATCGCCMGGAGATCGAGCT-3', which is called HSPF 3 and is shown in SEQ ID NO: 55. The backward primer is 5'-MGGTGCCGCGGATCTTGTT-3', which is called HSPR 4 and is shown in SEQ ID NO: 56. The positions of the hsp 65 gene fragment and the primers are schematically indicated in FIG. 1.

The present invention provides polynucleotides of hsp 65 gene fragments used for detecting or identifying mycobacterial species. In addition, the present invention provides polynucleotide sets comprising at least a polynucleotide selected from the group consisting of hsp 65 gene fragments or complementary sequences thereto.

The chronometer molecule used for the identification of mycobacterial species in the present invention is the 644-bp gene fragment located at the 163rd position to the 806th position of a 1623-bp hsp 65 gene of *M. tuberculosis*. The 644-bp gene fragment is substantially a 604-bp fragment because the 40-bp primer sequence is excluded. As a result of a Genbank database search, it was found that all 604-bp gene fragments of hsp 65 of 54 kinds of reference mycobacterial species are novel.

To establish the database for detecting and identifying the *mycobacteria*, the reference strains as shown in Table 1 were employed. 50 reference strains included 47 reference strains from the American Type Culture Collection (ATCC), a reference strain of *M. leprae* (Thai 53 strains) from Hanssen's disease center of the Catholic University of Korea, and 2 reference strains (type II, III) of *M. kansasii* from V. Vincent. In addition, hsp 65 gene fragments of 3 reference strains of *Tsukamurella* from the German Collection of Microorganisms and Cell Cultures, and a reference strain of *Nocardia* from ATCC were analyzed (Table 1).

TABLE 1

Reference strains of the present invention

| No | species | source |
|---|---|---|
| | Reference strains of mycobacteria | |
| 1 | M. abscessus | CAP97E-03 |
| 2 | M. africanum | ATCC 25420 |
| 3 | M. asiaticum | ATCC 25276 |
| 4 | M. aichiense | ATCC 27280 |
| 5 | M. avium | ATCC 25291 |
| 6 | M. bovis | ATCC 19210 |
| 7 | M. bovis BCG | French strain |
| 8 | M. celatum Type I | ATCC 51131 |
| 9 | M. celatum Type II | ATCC 51130 |
| 10 | M. chelonae | ATCC 35749 |
| 11 | M. chitae | ATCC 19627 |
| 12 | M. microti | ATCC 19422 |
| 13 | M. flavescens | ATCC 14474 |
| 14 | M. fortuitum 6841 | ATCC 6841 |
| 15 | M. fortuitum 49403 | ATCC 49403 |
| 16 | M. fortuitum 49404 | ATCC 49404 |
| 17 | M. gastri | ATCC 15754 |
| 18 | M. genavense | ATCC 51233 |
| 19 | M. gordonae | ATCC 14470 |
| 20 | M. haemophilum | ATCC 29548 |
| 21 | M. interjectum | ATCC 51457 |
| 22 | M. intermedium | ATCC 51848 |
| 23 | M. intracellulare | ATCC 13950 |
| 24 | M. kansasii Type I | ATCC 12478 |
| 25 | M. kansasii Type II | V. Vincent |
| 26 | M. kansasii Type III | V. Vincent |
| 27 | M. leprae | Thai 53 |
| 28 | M. malmoense | ATCC 29571 |
| 29 | M. marinum | ATCC 927 |
| 30 | M. mucogenicum | ATCC 49650 |
| 31 | M. neoaurum | ATCC 25795 |
| 32 | M. nonchromogenicum | ATCC 19530 |
| 33 | M. paratuberculosis | ATCC 19698 |
| 34 | M. phlei | ATCC 11758 |
| 35 | M. peregrinum | ATCC 14467 |
| 36 | M. scrofulaceum | ATCC 19981 |
| 37 | M. senegalense | ATCC 35796 |
| 38 | M. shimoidei | ATCC 27962 |
| 39 | M. simiae | ATCC 25275 |
| 40 | M. smegmatis | ATCC 19420 |
| 41 | M. szulgai | ATCC 35799 |
| 42 | M. terrae | ATCC 15755 |
| 43 | M. thermoresitibile | ATCC 19527 |
| 44 | M. triviale | ATCC 23292 |
| 45 | M. tuberculosis | ATCC 27294 |
| 46 | M. ulcerans | ATCC 19423 |
| 47 | M. vaccae | ATCC 15483 |
| 48 | M. wolinskyi | ATCC 700010 |
| 49 | M. parafortuitum | ATCC 19686 |
| 50 | M. farcinogenes | ATCC 35753 |

TABLE 1-continued

Reference strains of the present invention

| No | species | source |
|---|---|---|
| | Reference strain of bacteria other than mycobacteria | |
| 1 | T. paurometabola | DSM 20162 |
| 2 | T. tyrosinosolvens | DSM 44234 |
| 3 | T. pulmonis | DSM 44142 |
| 4 | N. carnea | ATCC 6847 |

For detecting and identifying mycobacterial species, the present invention provides 604-bp hsp 65 gene fragments as a new chronometer molecule, instead of 16S rDNA. The chronometer molecules must satisfy the following requirements in order to reflect the phylogenetic relationship. Firstly, the target gene must be essential for the functions and be highly conserved in all organisms. Secondly, the target gene must not mutate by lateral transfer based on selection pressure between species. Thirdly, the target gene must have interspecies variation and intraspecies conservation, which suitably reflects a phylogenetic relationship. The hsp 65 gene fragment of the present invention suitably satisfies the requirements of the chronometer molecule.

The nucleotide sequences of reference strains were analyzed according to a direct sequence analysis method, and compared with each other by multi-alignment. As a result, it was found that strains other than five kinds of TB complex including *M. africanum, M. bovis, M. bovis* BCG, *M. microti*, and *M. tuberculosis* (54 reference strains) have different nucleotide sequences, namely interspecies variation. In a previous report, the five kinds of *mycobacteria* belonging to the TB complex had the same nucleotide sequence analyzed according to another analyzing method using the 16S rDNA or rpoB gene fragment, and it was found that the mycobacterial species belonged to the same species. The result showed that the hsp 65 gene fragment of the present invention satisfied the interspecies variation of nucleotide sequences. Secondly, all 54 reference strains used in the experiment have 604-bp coding sequences without insertion and deletion, when they are multi-aligned. That is, there is no gap on multi-aligned sequences. 16S rDNA has a gap at a high frequency on multi-alignment of the nucleotide sequence. It is known that because an aligned gene corresponding to the gap must be eliminated in performing multi-alignment, the gap causes an error in establishing the phylogenetic tree at a high rate. Therefore, the identification method using the hsp 65 gene of the present invention provides significant advantages.

In order to investigate whether the 604-bp hsp 65 gene fragment of the present invention can be suitable for use as a chronometer molecule, a phylogenetic tree was constructed by the nucleotide sequence of 604-bp hsp 65 gene fragments of various *mycobacteria*. In addition, the *mycobacteria* identified according to the other conventional method were analyzed by the identification method of the present invention using the hsp 65 gene fragment. As a result, the present invention accurately identified the *mycobacteria*.

Figure 6:
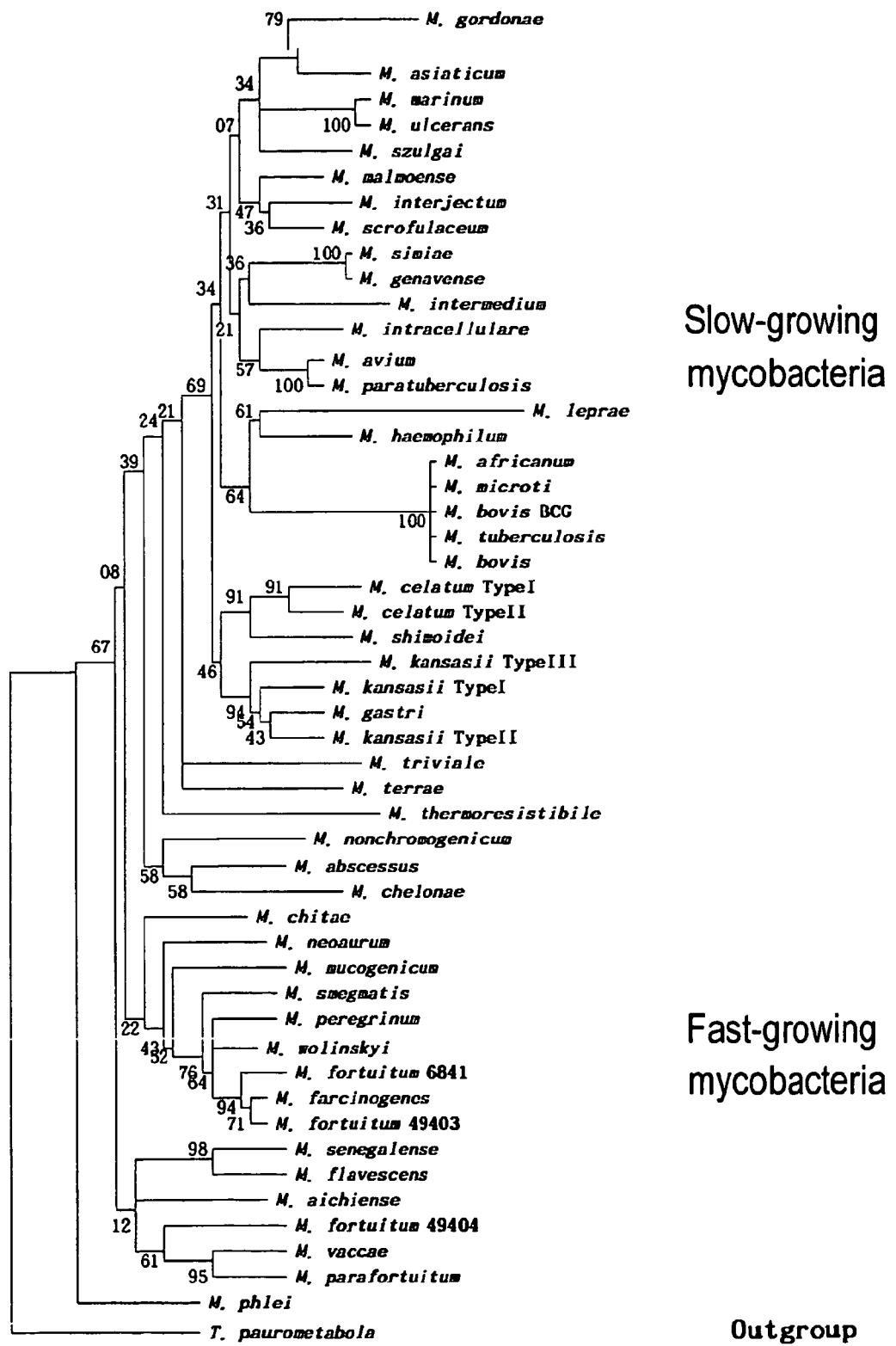
FIG. 6 shows phylogenetic relationships of 50 reference mycobacterial species obtained in Example 7.

The phylogenetic tree of the reference strains of the present invention showed the natural relationships of the *mycobacteria*. That is, the result confirmed that 50 reference strains of TB complex formed a large group excluding *T. paurometabola* as an outgroup (FIG. 6). Also, slow-growing *mycobacteria* and fast-growing *mycobacteria* formed different groups. *M. tuberculosis* and *M. leprae* of pathogenic *mycobacteria* formed the same branch of the phylogenetic tree.

MOTT were isolated frequently. *M. avium* and *M. intracellulare*, showing quite similar biochemical characteristics, formed the same branch. The results showed general characteristics of *mycobacteria*. *M. kansasii* and *M. gastri* have 100% sequence homology, and thus cannot be differentiated according to the conventional identification method using 16S rDNA, but they are differentiated according to the present invention. Moreover, the subspecies of *M. kansasii* can be differentiated (namely, the hsp 65 gene fragments of *M. kansasii* Type I, II, and III have different nucleotide sequences). The results of the present invention show the phylogenetic relationships of *mycobacteria*. That is, the slow-growing *mycobacteria* and fast-growing bacteria form different branches of the phylogenetic tree, and *M. tuberculosis* and *M. lepare* form the same branch.

The mycobacterial species can be identified according to the identifying method of *mycobacteria*, such as comparative sequence analysis, probe hybridization, and PCR-RFLP, using the polynucleotide of the present invention. The comparative sequence analysis, probe hybridization, and PCR-RFLP can be carried out according to the method which has been known to a skilled person in the art. For example, a method for identifying the *mycobacteria* with 16s rDNA can be applied for the identification method of the present invention.

In one aspect, the present invention provides a method for the identification of *mycobacteria* by using PCR-RFLP (also called PRA). The method comprises the steps of amplifying hsp 65 gene fragments of *mycobacteria* with primers specific to *mycobacteria*, preferably primers as shown in SEQ ID NOs: 55 and 56, and analyzing the amplified product according to the RFLP analysis by using the restriction enzyme recognizing the target site located in the amplified product. The identification method is simple, economical, and specific to the *mycobacteria*.

The general PRA method comprises the steps of 1) DNA extraction, 2) PCR amplification, 3) confirmation of the amplified product, 4) digestion with a restriction enzyme, 5) analysis of restriction fragment, and 6) visualization by image capture systems. The restriction enzymes applicable for this invention include all the restriction enzymes that can recognize the site specifically existing in a 644-bp fragment, preferably Xho I.

In addition, any method for differentiating the restriction fragment on the basis of its size, preferably electrophoresis, and more preferably agarose gel electrophoresis or polyacrylamide gel electrophoresis, can be applied for analyzing the restriction fragment.

In comparison with the conventional method for identifying *mycobacteria* using the hsp 65 gene, the method of the present invention is simple and economical. The conventional method uses a 439-bp fragment of hsp 65 gene as a target gene, and two kinds of restriction enzymes, Hae II and BstE II. As described above, the identification method of the present invention uses one restriction enzyme, such as Xho I, and it is advantageous in time and cost. In addition, the 439-bp fragment of the conventional method is shorter than 644-bp of the present invention. By treating with Hae III and recognizing four nucleotides in the conventional method, many fragments are produced so that the small fragments, such as a 10-bp fragment, must be separated. Thus, in order to accurately identify *mycobacteria* in the conventional method, it is necessary to use the restriction fragment database of reference strains, or to analyze the *mycobacteria* of interest together with putative reference species according to restriction enzyme treatment and electrophoresis. In the preferred embodiment of the present invention, the identifying method of *mycobacteria* uses Xho-I recognizing six (6) nucleotides as target sites, thereby making it perform more gel electrophoresis. However, the identification method is accurate and simple.

The present invention provides a new system where a 644-bp hsp 65 gene fragment of *mycobacteria* is amplified with primers specifically for amplifying the 644-bp hsp 65 gene fragment of *mycobacteria*, and it is treated with Xho-I to differentiate and identify the mycobacterial species. Only a process of PRA makes it possible to differentiate the MOTT into 3 groups, as well as *M. tuberculosis*. That is, the treatment of the amplified product with a restriction enzyme produces only a 644-bp gene fragment in fast-growing *mycobacteria*, thereby differentiating it from the slow-growing *mycobacteria*. *M. avium* complex (for examples, *M. avium* and *M. intracellulare*) which belongs to slow-growing *mycobacteria* and is isolated most frequently in clinical samples produces three kinds of restriction fragments, 391-bp, 169-bp, and 84-bp, thereby differentiating them from other groups including *M. kansasii* producing two kinds of restriction fragments, 391-bp and 253-bp.

Among the genus *Mycobacterium* that includes about 70 species, about 10 strains including *M. tuberculosis*, *M. avium* complex, *M. kansasii*, *M. szulgai*, *M. gordonae*, *M. fortuitum*, and *M. chelonae* cover 90% of isolates in a clinical sample, and thus they can be effectively identified according to the identification method of the present invention.

In another aspect of the present invention, a TB complex can be differentiated from MOTT by treating the amplified hsp 65 gene fragment with Xho I, and analyzing it according to RFLP. In addition, the TB complex can be differentiated based on the restriction fragment of the amplified 644-bp hsp 65 fragments of 391-bp, 150-bp, and 103-bp.

In a further aspect of the present invention, a 644-bp hsp 65 gene fragment of fast-growing *mycobacteria* is not cleaved by a restriction enzyme, Xho I. The fast growing *mycobacteria* can be differentiated depending on whether the amplified product can be cleaved by the restriction enzyme or not. Thus, the present invention provides a method for differentiating fast-growing *mycobacteria* among MOTT. When 391-bp, 169-bp, and 84-bp restriction fragments are produced by the treatment of Xho I and RFLP analysis of *mycobacteria*, the *mycobacteria* can be identified as species including *M. avium*, *M. intracellulare*, *M. celatum*, *M. shimoidei*, and *M. szulgai*.

In the case that the treatment of Xho I and the RFLP analysis produces 391-bp and 253-bp restriction fragments, the mycobacterial species are identified as species including *M. gastri*, *M. genavense*, *M. gordonae*, *M. haemophilum*, *M. kansasii*, *M. malmoense*, *M. marinum*, *M. scrofulaceum*, *M. simiae*, and *M. ulcerans*.

Figure 4:
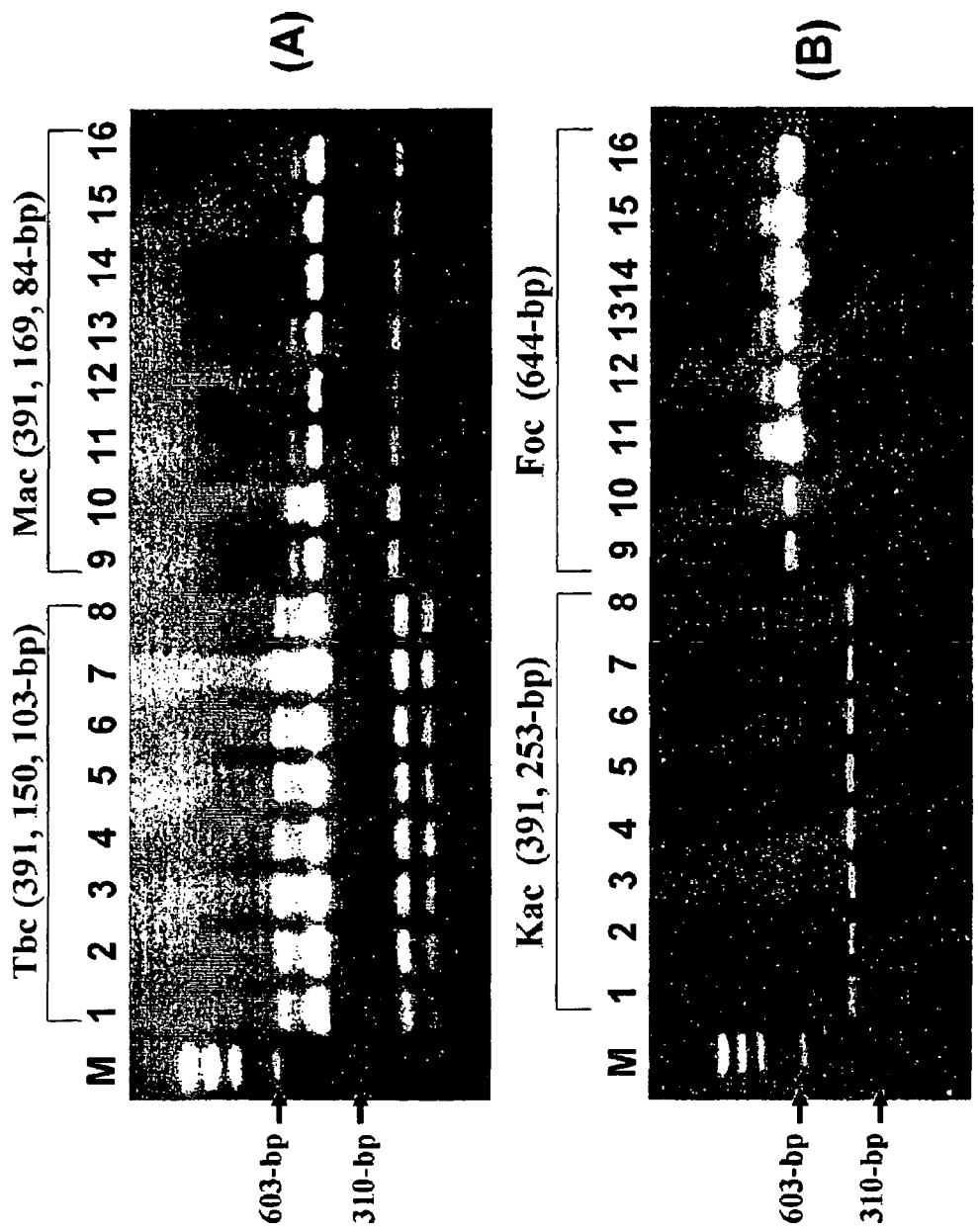
FIG. 4 is a summarized diagram showing a result of PCR-RFLP of hsp 65 gene fragments of reference strains of *mycobacteria*.

The differentiation results are summarized, depending on the size pattern of restriction fragments obtained in the present invention, in FIG. 4.

The present invention also relates to a kit for differentiating or diagnosing mycobacterial species comprising Xho I and primers specific to the hsp 65 gene of mycobacterial species, preferably primers as shown in SEQ ID NOs: 55 and 56, wherein the DNA of mycobacterial species in a sample is amplified with the primers to produce the hsp 65 gene fragment, and the mycobacterial species are differentiated depending on the restriction fragments obtained according to RFLP. The kit further comprises a PCR amplification kit and a RFLP kit. Any kit that has been known for the use and is commercially available is applicable to the present invention.

In another aspect, the present invention relates to a method for detecting and identifying the mycobacterial species, comprising the steps of (1) amplifying 604-bp hsp 65 gene fragments of mycobacterial species of interest with a primer that can specifically amplify hsp 65 gene fragments, (2) hybridizing the amplified product with a probe set comprising at least a 604-bp hsp 65 gene fragment selected from the group consisting of the polynucleotide of a 604-bp hsp 65 gene fragment of mycobacterial species. In the embodiment of the method, the hsp 65 gene fragment of mycobacterial species of interest can be amplified according to general amplification methods of nucleotides such as PCR, LCR (ligase chain reaction), NASBA, etc. The amplified product can be hybridized with 604-bp gene fragment(s) or 644-bp gene fragment(s) of the reference species, preferably a probe or probe set comprising a fragment selected from the group consisting of polynucleotides as shown in SEQ ID NO: 1 to SEQ ID NO: 54, and the polynucleotides complementary thereto. The hybridization step can be carried out according to a general hybridization method. For example, the hybridization can be performed on a solid surface, or it can be carried out by using a microarray including the probe immobilized thereon.

The present invention provides an identification or diagnosis kit comprising (1) a means for amplification including a pair of primers specific to an hsp 65 gene of mycobacterial species; (2) a means for hybridization comprising a 604-bp or 644-bp gene fragment of hsp 65 of mycobacterial species, preferably a probe or probe set comprising a gene fragment selected from the group consisting of polynucleotides as shown in SEQ ID NO: 1 to SEQ ID NO: 54 and polynucleotides complementary thereto; and (3) a labeling means for detecting the hybridized product. The labeling means can include all the labeling means that can be generally used for detection of hybridized DNA, for example Cy5, biotin-binding compounds, Cy3, EDANS(5-(2'-aminoethyl)amino-1-naphthalene sulfate), tetramethylrhodamine (TMR), tetramethylrhodamine isocyanate (TMRIT C), x-rhodamine, and Texas red.

The present invention provides a method for identification of mycobacterial species by using comparative sequence analysis. The database of hsp 65 gene fragments as described above can be applicable to the method. The present invention provides a method for identification of mycobacterial species by using 604-bp hsp 65 gene fragments. More specifically, the method comprises the steps of:

(1) amplifying hsp 65 gene fragments of *mycobacteria* of interest with primers for specifically amplifying the hsp 65 gene of *mycobacteria*;

(2) analyzing the nucleotide sequence of the amplified hsp 65 gene fragment; and (3) comparing the nucleotide sequence of the amplified hsp 65 gene fragment obtained in step (2) with a 604-bp hsp 65 gene fragment of a reference strain of *mycobacteria*.

Preferably, step (3) can be carried out by multi-aligning the 604-bp hsp 65 gene fragment of mycobacterial species of interest with a polynucleotide set comprising at least an hsp 65 604-bp polynucleotide of reference strains of *mycobacteria* to infer a phylogenetic tree. According to the comparative sequence analysis, a database of 604-bp hsp 65 gene fragments is established by amplifying the hsp 65 gene fragment of reference species of *mycobacteria* with the primers specific to *mycobacteria*, preferably primers as shown in SEQ ID NO: 55 and SEQ ID NO: 5, and analyzing the nucleotide sequence of the amplified product. In the example of the present invention, the database of 604-bp fragments of 54 reference strains except for the primer sequence is established by analyzing the nucleotide sequences of the 604-bp fragments, and through multi-alignment. The 604-bp fragments of reference strains obtained in the present invention are shown in SEQ ID NO: 1 to SEQ ID NO: 54. The mycobacterial species of interest can be identified according to comparative sequence analysis by using the database.

As the hsp 65 gene fragments of the mycobacterial species of interest are different from those of the reference species, mycobacterial species of interest can be identified based on the criterion of nucleotide sequence homology of hsp 65 genes of reference species. Because a mycobacterial species has a different range of sequence homology, mycobacterial species can be identified based on the specific range of the sequence homology thereof. For example, *M. gordonae* has a wide range of sequence homology, but *M. tuberculosis* has a narrow range. In addition, mycobacterial species can be identified by multi-aligning the nucleotide sequence of 604-bp hsp 65 gene fragments with those of reference species to infer a phylogenetic relationship.

To confirm that the database including 604-bp hsp 65 gene fragments of 50 reference strains of mycobacterial species can be useful for identifying the mycobacterial species in a clinical sample, the identification method of the present invention was applied for 38 strains of *mycobacteria* obtained from the Korean Institute of Tuberculosis of the Korean National Tuberculosis Association, which had already been identified by using biochemical identification methods such as pigmentation on solid media; optimal growth temperature; degree of growth on media including catalase, iron, and p-nitrobenzoic acid; hydrolysis of tween 80; a Tellulite reduction test; degree of growth on media including 5% NaCl; production of Niacin; Nitrate reduction test; and production of Urease according to a blind test. The test results are shown in Table 2. In the table, the strain item indicates the number offered by the Korean Institute of Tuberculosis at random. The biochemical method item is a result of identification by the Korean Institute of Tuberculosis, and the item hsp 65 gene analysis method is a result of the present invention.

TABLE 2

Identification result for clinical isolates

| No. | strain | Biochemical method | hsp 65 gene analysis method |
|---|---|---|---|
| 1 | KIT 77009 | *M. tuberculosis* | *M. tuberculosis* |
| 2 | KIT 77710 | *M. tuberculosis* | *M. tuberculosis* |
| 3 | KIT 77712 | *M. tuberculosis* | *M. tuberculosis* |
| 4 | KIT 77714 | *M. tuberculosis* | *M. tuberculosis* |
| 5 | KIT 77719 | *M. tuberculosis* | *M. tuberculosis* |
| 6 | KIT 77720 | *M. tuberculosis* | *M. tuberculosis* |
| 7 | KIT 77721 | *M. tuberculosis* | *M. tuberculosis* |
| 8 | KIT 77722 | *M. tuberculosis* | *M. tuberculosis* |
| 9 | KIT 77723 | *M. tuberculosis* | *M. tuberculosis* |
| 10 | KIT 77725 | *M. tuberculosis* | *M. tuberculosis* |
| 11 | KIT 41105 | *M. avium* complex | *M. intracellulare* |
| 12 | KIT 41110 | *M. avium* complex | *M. avium* |
| 13 | KIT 41111 | *M. avium* complex | *M. intracellulare* |
| 14 | KIT 41115 | *M. avium* complex | *M. intracellulare* |
| 15 | KIT 30101 | *M. scrofulaceum* | *M. scrofulaceum* |

TABLE 2-continued

Identification result for clinical isolates

| No. | strain | Biochemical method | hsp 65 gene analysis method |
|---|---|---|---|
| 16 | KIT 30102 | M. scrofulaceum | M. scrofulaceum |
| 17 | KIT 20118 | M. kansasii | M. kansasii Type I |
| 18 | KIT 20119 | M. kansasii | M. kansasii Type I |
| 19 | KIT 20120 | M. kansasii | M. kansasii Type I |
| 20 | KIT 47101 | M. terrae complex | M. nonchromogenicum |
| 21 | KIT 47102 | M. terrae complex | M. nonchromogenicum |
| 22 | KIT 47103 | M. terrae complex | M. nonchromogenicum |
| 23 | KIT 47104 | M. terrae complex | M. nonchromogenicum |
| 24 | KIT 32101 | M. gordonae | M. gordonae |
| 25 | KIT 32104 | M. gordonae | M. gordonae |
| 26 | KIT 32105 | M. gordonae | M. gordonae |
| 27 | KIT 32106 | M. gordonae | M. gordonae |
| 28 | KIT 31102 | M. szulgai | M. szulgai |
| 29 | KIT 31103 | M. szulgai | M. szulgai |
| 30 | KIT 31106 | M. szulgai | M. szulgai |
| 31 | KIT 31107 | M. szulgai | M. szulgai |
| 32 | KIT 21101 | M. marinum | M. marinum |
| 33 | KIT 60108 | M. fortuitum complex | M. fortuitum 6841 |
| 34 | KIT 60109 | M. fortuitum complex | M. fortuitum 6841 |
| 35 | KIT 60110 | M. fortuitum complex | M. fortuitum 6841 |
| 36 | KIT 60111 | M. fortuitum complex | M. fortuitum 6841 |
| 37 | KIT 61104 | M. chelonae complex | M. abscessus |
| 38 | KIT 61105 | M. chelonae complex | M. abscessus |

The nucleotide sequences of 38 *mycobacteria* obtained from the clinical sample were analyzed and then multi-aligned with the database of reference strains to infer the phylogenetic tree. From the results, all 38 strains were identified to the species level with 100% sensitivity and specificity (Table 2 and FIGS. 7A to 7D). The results are specifically described below.

A. Identification of *M. tuberculosis*

*M. tuberculosis* is the most pathogenic and important species in public health. The results of the identification of *M. tuberculosis* by using the database of the reference species of *mycobacteria* of the present invention confirmed that all twenty (20) *M. tuberculosis* were identified (Table 2 and FIG. 7c), and showed that 604-bp hsp 65 gene fragments of 20 strains have 100% sequence homology with a 604-bp fragment of *M. tuberculosis* ATCC 27284 reference strain. The 16s rDNA and rpoB gene used as a target gene are involved in resistance to streptomycin and to rifampin, respectively. The target genes in *mycobacteria* with a resistance to antituberculosis drugs can be mutated. However, unlike 16s rDNA and rpoB, the hsp 65 gene is not related to resistance to antibiotics, and thus it does not mutate. Therefore, the 604-bp hsp 65 gene is stable with respect to the selection pressure of antituberculosis drugs in comparison with other target genes.

B. Identification of *M. avium* Complex

The identification method was applied to 4 strains of *M. avium* complex which are the most commonly isolated in MOTT. As a result, the strains were identified to the species level as 3 *M. intracellulares* and a strain of *M. avium*. According to the biochemical identification method, it is not possible to differentiate *M. intracellulare* and *M. avium* because they have the same biochemical characteristics. In comparing the nucleotide sequences of 1 *M. avium* (KIT 41110) and *M. avium* ATCC 25281, they have 99.5% nucleotide sequence homology with 3 different nucleotides. When the nucleotide sequences of the 3 *M. intracellulares* (KIT 41105, 41111, and 51115) are compared with that of *M. Intracellulare* ATCC 13850, they show 99.0-99.8% sequence homology. Those results are consistent with the fact that *M. intracellulare* includes various genotypes, namely interspecies heterogeneity (Devallois A, Picardeau M, Paramasivan C N, Vincent V, Rastogi N: Molecular characterization of *Mycobacterium avium* complex isolates giving discordant results in Accu-Probe tests by PCR-restriction enzyme analysis, 16s rRNA sequencing, and DT1-DT6 PCR. *J Clin Microbiol* 1997 35: 2767-2772).

C. Identification of *M. scrofulaceum*.

2 strains (KIT 30101, 30102) were identified as *M. scrofulaceum* (FIG. 7B), and they have 99.8-100% nucleotide sequence homology with *M. scrofulaceum* ATCC 19981.

D. Identification of *M. kansasii*

*M. kansasii* is the most pathogenic in MOTT, and it is in second position in isolation frequency after *M. avium* complex. 16s rDNA of *M. kansasii* showed 100% nucleotide sequence homology with that of non-pathogenic *M. gastri*, thereby making it difficult to differentiate them. In addition, *M. kansasii* consists of at least 5 subspecies where type II and type III are reported to be separated from clinical material. 3 strains are identified as *M. kansasii* by using the database of 604-bp hsp 65 gene fragments of reference strains, which are consistent with results of the biochemical identification method. The method for identifying the mycobacterial species by using the database has characteristics such that *M. kansasii* can be differentiated from *M. gastri*, and subspecies of *M. kansasii* can be differentiated. The result confirmed that 3 strains of *M. kansasii* (KIT 20118, 20119, 20120) have 100% nucleotide sequence homology, and they are identified as *M. kansasii* Type I ATCC 12478 (FIG. 4c).

Figure 7A:
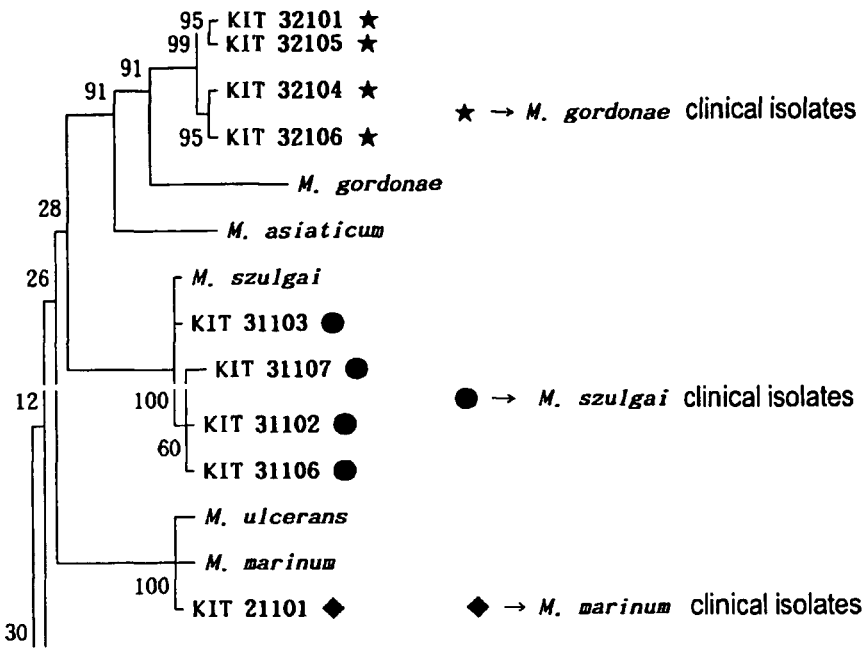
FIGS. 7A to 7D shows the results of the identification of *mycobacteria* in a clinical sample according to a comparative sequence analysis.

E. Identification of *M. gordonae. M. szulgai, M. marinum*, and *M. terrae* Complex As a result of identifying the clinically separated mycobacterial strains with the database of the present invention, 4 strains (KIT 32101, 32104, 32105, and 32106) were found to be *M. gordonae* (FIG. 7A, and Table 2). When comparing the nucleotide sequences of the 604-bp hsp 65 gene fragments of the 4 strains, they have 99.2-99.8% sequence homology with each other, but they have 95.9-96.3% sequence homology with *M. gordonae* ATCC 14470, which indicates a considerably low sequence homology between *M. gordonae* species. The result is consistent with the report that *M. gordonae* has intraspecies heterogeneity (Abed Y, Bollet C, de Micco P. Identification and strain differentiation of *Mycobacterium* species on the basis of DNA 16S-23S spacer region polymorphism. Res Microbiol. 1995 146(5): 405-13). That is, 4 isolates obtained from the same region have high sequence homology with one another, but low sequence homology with reference strains obtained from different regions.

As a result of identification of mycobacterial species with the database of reference species, 4 strains (KIT 31102, 31103, 31106, and 31107) were identified as *M. szulgai*, which is consistent with that of the biochemical identification method (FIG. 7A, and Table 2). The nucleotide sequences of the 4 strains have 99.5-100% nucleotide sequence homology with *M. szulgai* ATCC 35799.

As a result of identification of mycobacterial species with the database of reference species, 1 strain was identified as *M. marinum*, which is consistent with that of the biochemical identification method (FIG. 7A and Table 2). The nucleotide sequence of the strain has 99.3% nucleotide sequence homology with *M. marinum* ATCC 927(//).

*M. terrae* complex does not generally cause disease in humans, and it includes 3 reference strains of the present invention (*M. terrae, M. triviale, M. nonchromogenicum*), and various mycobacterial species which are not classified. As a result of identification of mycobacterial species with the database of reference species, 4 strains were identified as *M. nonchromogenicum* among the *M. terrae* complex, which is consistent with the previous report using the biochemical identification method. When comparing the 4 strains with the reference strain, the nucleotide sequences of the strains had 95.0-100% nucleotide sequence homology with *M. nonchromogenicum* ATCC 19530. The result concurs with the report that *M. terrae* complex has intraspecies heterogeneity.

F. Identification of Fast-growing *Mycobacteria* (*M. fortuitum* Complex and *M. chelonae* Complex)

As a result of identification of mycobacterial species with the database of reference species, 2 strains (KIT 61104, 61105) were identified as *M. abscessus* of *M. chelonae* complex. The result is consistent with that of the biochemical identification method. However, the identification method of the present invention resolves the problem of the conventional biochemical method that *M. chelonae* and *M. abscessus* cannot be differentiated. The nucleotide sequences of the hsp 65 gene fragments of the strains have 98.4-99.5% nucleotide sequence homology with *M. abscessus* CAP97E-03.

According to the identification method of the present invention, 4 strains are identified as *M. fortuitum*, which is consistent with the result of the biochemical identification method. *M. fortuitum* complex covers various mycobacterial species, and includes *M. fortuitum* ATCC 6841, *M. fortuitum* ATCC 49403, *M. fortuitum* ATCC 49404, and *M. peregrinum* as reference species. 4 clinically isolated strains were identified as *M. fortuitum* ATCC 6841. When the 4 strains are compared with *M. fortuitum* ATCC 6841, they have 99.4-100% nucleotide sequence homology.

The present invention is further specifically illustrated in the following examples, which should not be taken to limit the scope of the invention.

EXAMPLE 1

DNA Isolation from Reference Strains and Clinically Isolated Strains 1-1: Selection of Subject Strain As shown in Table 1, The hsp 65 gene fragments of 50 reference strains were sequenced, including 47 reference strains from the American Type Culture Collection (ATCC), a reference strain of *M. leprae* (Thai 53 strain) from Hanssen's disease center of the Catholic university of Korea, and 2 reference strains (type II, III) of *M. kansasii* from V. Vincent. In addition, 3 reference strains of *Tsukamurella* from the German Collection of Microorganisms and Cell Cultures and a reference strain of *Nocardia* from ATCC were selected.

As shown in Tables 2 and 4, the clinically isolated strains are strains that were previously identified according to the biochemical identification method.

1-2: DNA Isolation

The genomic DNA of reference strains and clinically isolated strains was extracted according to the Bead Beater Phenol (BB/P) extraction method. The culture of each *mycobacteria* was suspended with TEN buffer (10 mM Tris-HCl, 1 mM EDTA, 100 mM NaCl: pH 8.0) placed in a 2.0 ml screw-cap microcentrifuge tube filled with 100 µl (packed volume) of beads (glass beads, 0.1 mm diameter; Biospec Products, Bartlesville, Okla., U.S.A.) and 100 A phenol:chloroform:isopropylalcohol solution (50:49:1, v/v/v). To disrupt the bacteria, the tube was oscillated with a Mini-Bead beater (Biospec Products, Bartlesville, Okla., U.S.A.) for one minute, and to separate phases, the tube was centrifuged (12,000 rpm, 5 min). After the supernatant (100 µl) was transferred into another clean tube, the tube was centrifuged at 15,000 rpm for 5 min with the addition of 60 µl of isopropyl alcohol. The resultant DNA pellet was washed with 70% ethanol, solubilized with 60 µl of TE buffer (10 mM Tris-HCl, 1 mM EDTA), and used as a template DNA for the analysis of nucleotide sequence and identification of the mycobacterial species in the following Examples.

EXAMPLE 2

Preparation of Primers for Amplifying hsp 65 Gene Fragments

A forward primer and a backward primer were prepared for specifically amplifying hsp 65 genes of all mycobacterial species. hsp 65 genes of *M. tuberculosis* (GenBank No. M15467) and *M. avium* (GenBank No. AF281650) of which 623-bp full sequences were previously analyzed for another purpose, and *T. paurometabola* (GenBank No. AF352578) were used for this example to prepare primers for amplifying hsp 65 genes of all the *mycobacteria*. The primers were shown in SEQ ID NO: 55 and 56, and positions thereof are indicated in FIG. 1.

```
Forward primer: HSPF3
5'-ATCGCCAAGGAGATCGAGCT-3'      (SEQ ID NO: 55)

Backward primer: HSPR4
5'-AAGGTGCCGCGGATCTTGTT-3'      (SEQ ID NO: 56)
```

EXAMPLE 3

Amplification of 644-bp hsp 65 Gene Fragment 3-1) PCR Amplification of hsp 65 Gene PCR reaction was carried out using AccuPower PCR Pre-Mix (Korea, bioneer) containing 2 U Taq polymerase, 10 mM dNTP, 10 mM Tris-HCl (pH 8.3), and 1.5 mM $MgCl_2$. 50 ng of each DNA isolated in Example 1, and 20 pmol of each primer prepared in Example 2 were placed in a tube and distilled water was added thereto to a final volume of 20 µl. PCR was performed at 95° C. for 5 min for a first denaturation followed by 30 cycles of 1 min at 95° C. for subsequent denaturation, 45 s at 62° C. for annealing, 1 min 30 s at 72° C. for extension, and 5 min at 72° C. for final extension (Model 9600 thermocycler, Perkin-Elmer cetus). After PCR reaction, PCR products were electrophoresed on 1% agarose gel to observe a 644-bp fragment.

3-2) Separation of PCR Product

After electrophoresis on 1% gel, a gel part containing the 644-bp of PCR product was cut and transferred into a new tube in order to separate DNA. DNA isolation and purification were carried out using a Qiaex (Qiagen, Germany) system. 500 µl of a solution for gel dissolution, QX1, was added to the tube, and the gel and solution were melted at 50° C. for 15 min. Then, 10 μl of gel beads were mixed therein and held at 50° C. for 15 min. The tube was subjected to a vortex for 10 s at intervals of 1 min to equally spread the beads. The tube contents were then washed once with QX1 and twice with QF, dried at 45° C. for 10 min, followed by addition of a TE buffer to obtain 20 μl of DNA.

Figure 2:
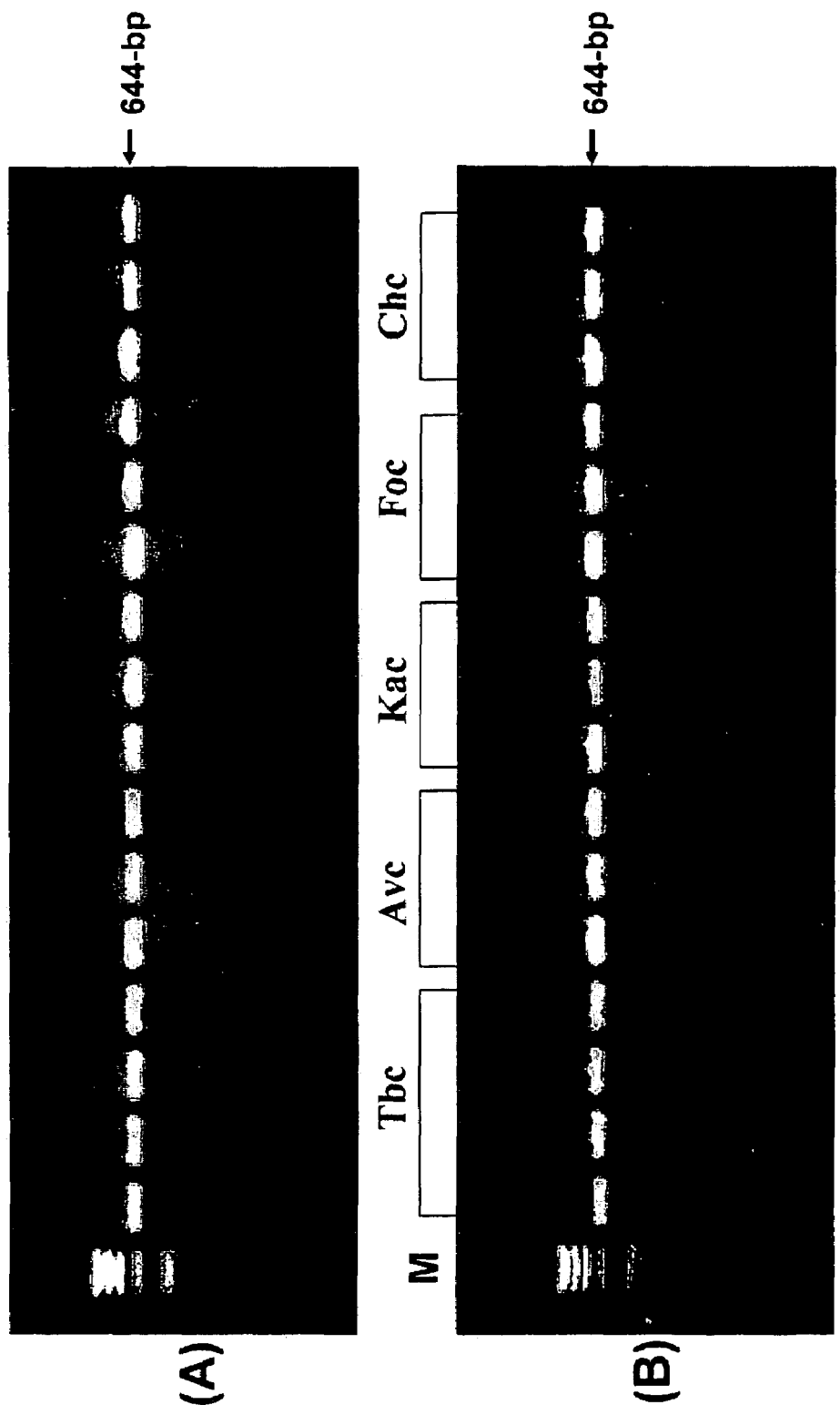
FIG. 2 is a photograph of electrophoresis showing the amplified product of mycobacterial DNA, wherein panel A shows a result obtained from analysis of the amplified gene fragment of reference strains, and panel B shows a result for the amplified gene fragments of *mycobacteria* in a clinical sample.

After PCR reaction, 1% agarose gel electrophoresis confirmed that a 644-bp fragment was obtained, which is shown in FIG. 2.

Panel A in FIG. 2 indicates amplified DNA products of reference strains as follows.

Lane M: DNA size marker obtained by treating 174 with Hae III;
1: *M. tuberculosis*, 2: *M. bovis*,
3: *M. africanum*, 4: *M. avium*,
5: *M. intracellulare*, 5: *M. scrofulaceum*,
6: *M. gordonae*, 7: *M. szulgai*,
8. *M. marinum*, 9: *M. ulcerans*,
10: *M. celatum* Type I, 11. *M. genavense*,
12. *M. malmoense*, 13. *M. fortuitum* 6841,
14: *M. abscessus*, 15: *M. chelonae*,
16: *M. peregrinum*.

Panel B in FIG. 2 indicates amplified DNA products of clinically isolated strains as follows.

lane M: DNA size marker obtained by treating 174 with HaeIII;
1-4: Tbc—clinically isolated strain of *M. tuberculosis*
5-7: Mac—clinically isolated strain of *M. avium* complex;
8-10: Kac—clinically isolated strain of *M. kansasii;*
11-13: Foc—clinically isolated strain of *M. fortuitum;*
14-16: Chc—clinically isolated strain of *M. chelonae.*

As shown in FIG. 2, 644-bp hsp 65 gene fragments were obtained from reference strains and clinically isolated strains used in the Example. Therefore, the result suggests that the primers of the present invention could amplify the hsp 65 gene of all the *mycobacteria*.

EXAMPLE 4

Nucleotides Sequence Analysis of hsp 65 Gene Fragment 4-1: Sequence Analysis

Two strands of 604-bp hsp 65 gene fragments except for 40-bp of primer region which corresponded to the $183^{rd}$ to $806^{th}$ positions in hsp 65 of *M. tuberculosis* were sequenced with a forward primer (HSPF3) and a backward primer (HSPR4). The eluted DNA from the gel was used as a template, and automatic sequencing was performed. 1060 ng of the template DNA, 1.2 pmol of each primer, and 2 μl of dye from a BigDye Terminator Cycle Sequencing kit (PE Applied Biosystems) were mixed, and distilled water were added thereto, to a final volume of 10 μl. Reaction was undertaken with a Perkin Elmer Cetus 9600 for 25 cycles of 10 sec at 95° C., 10 sec at 60° C., and 4 min at 60° C. DNA was purified from the reacted sample by an ethanol precipitation method. That is, after 180 μl of distilled water and 10 μl of 3 M sodium acetate were added to the sample to bring the total volume to 200 μl, twice the volume of 100% ethanol was mixed with the mixture and centrifuging was carried out to precipitate DNA. After adding 500 μl of 70% ethanol, centrifuging was carried out at 15,000 rpm for 20 min to wash the DNA. The DNA was recovered with formamide (PE Applied Biosystems). The purified DNA was incubated at 95° C. for 5 min to generate single strand DNA, and the sequence was analyzed with an ABI 3100 system (ABI3100, PE Applied Biosystems) after electrophoresis for 2 hours 30 min. From a search on Genbank, all 604-bp hsp 65 gene fragments of 54 reference strains were found to be novel.

4-2) Alignment of 604-bp hsp 65 Gene Fragment

The nucleotide sequences obtained in the examples were multi-aligned by using the Megalign program of the Dnastar software to construct a database of hsp 65 gene fragments.

The rpoB nucleotide sequence (606-bp) of 54 reference strains analyzed by EXAMPLE 4-2) were multi-aligned by using the Megalign program of the Dnastar software to construct a database of hsp 65 gene fragments.

For the multiple alignment, 604-bp nucleotides were translated to 301 amino acid residues and the amino acid residues were multiply aligned by a Clustal Method of the Megalign program. The database for identifying is the *Mycobacteria* was constructed using 604 bp nucleotides deduced from the aligned 301 amino acid residues. Sequence homology among nucleotide sequences of reference strains was determined by analyzing multiple aligned database with sequence distance on the Megalign program.

The nucleotide sequences of 54 reference strains were analyzed by using a direct sequence analysis method, and then multi-aligned. The result confirmed that other reference strains except for TB complex including *M. africanum, M. bovis, M. bovis* BCG, *M. microti*, and *M. tuberculosis* had different sequences.

4-3) Construction of Phylogenetic Tree

The phylogenetic relationship between reference strains was analyzed using a phylogenetic tree constructed by MEGA software (Kumar, S., K. Tamura, and N. Masatoshi. 1993. MEGA: molecular evolutionary genetics analysis, version 1.01. Pennsylvania State University, University Park). The multiple aligned 604-bp polynucleotides from 50 kinds of mycobacterial species were used to construct a Neighbor-joining phylogenetic tree based on the Juke-Cantor distance estimation method and a pairwise deletion method by using a 604-bp polynucleotide of *T. paurometabola* as a outgroup. An analysis of bootstrap was performed through 100 replications. 50 kinds of *mycobacteria* reference strains made a large group, and fast-growing *mycobacteria* and slow-growing *mycobacteria* were formed into different groups from each other. The result reflected the general characteristics of *mycobacteria* in that pathogenic *mycobacteria, M. tuberculosis*, and *M. leprae* were located in the same branch, and *M. avium* and *M. intracellulare* among MOTT were also formed in the same branch on the phylogenetic tree. In addition, the phylogenetic tree was characterized in that *M. kansasii* could be differentiated from *M. gastri*, which could not be differentiated according to the identification method using 16s rDNA. Also, subspecies of *M. kansasii* can be differentiated (that is, nucleotide sequences of Type I, II, and III of *M. kansasii* are different) (FIG. 6).

EXAMPLE 5

Differentiation of Reference Strains of *Mycobacteria* by Using the PRA

Xho-I (5'-CTCGAG-3') with 6 nucleotide recognition sites was determined by analyzing 644-bp (corresponding to the $163^{rd}$ to the $806^{th}$ position) of hsp 65 gene of *M. tuberculosis* (GenBank No. M15467) and *M. avium* (GenBank No. AF281650) with the Mapdraw program of Dnastar software.

10 ul of the 644-pb PCR product in EXAMPLE 3 of 27 kinds of reference strains as shown in Table 3 were transferred to a new test tube, treated with 1 ul (10 units) of Xho-I, and became a final volume of 20 ul with addition of 2 ul of 10× buffer and distilled water. The mixture was kept at 37° C. in a bath for 1 hour. The cleaved mixture was analyzed by 2% agarose gel electrophoresis in order to investigate whether the 27 kinds of reference strains could be identified.

TABLE 3

PRA analysis of 27 kinds of reference strains

| No. | strain | Source |
|---|---|---|
| | TB complex | |
| 1 | M. africanum | ATCC 25420 |
| 2 | M. bovis | ATCC 19210 |
| 3 | M. bovis BCG | French strain |
| 4 | M. tuberculosis H37Rv | ATCC 27294 |
| | Slow-growing mycobacteria | |
| 5 | M. avium | ATCC 25291 |
| 6 | M. celatum Type I | ATCC 51131 |
| 7 | M. celatum Type II | ATCC 51130 |
| 8 | M. gastri | ATCC 15754 |
| 9 | M. genavense | ATCC 51233 |
| 10 | M. gordonae | ATCC 14470 |
| 11 | M. haemophilum | ATCC 29548 |
| 12 | M. interjectum | ATCC 51457 |
| 13 | M. intracellulare | ATCC 13950 |
| 14 | M. kansasii Type I | ATCC 12478 |
| 15 | M. malmoense | ATCC 29571 |
| 16 | M. marinum | ATCC 927 |
| 17 | M. scrofulaceum | ATCC 19981 |
| 18 | M. shimoidei | ATCC 27962 |
| 19 | M. simiae | ATCC 25275 |
| 20 | M. szulgai | ATCC 35799 |
| 21 | M. ulcerans | ATCC 19423 |
| | Rapid-growing mycobacteria | |
| 22 | M. abscessus | CAP97E-03 |
| 23 | M. chelonae | ATCC 35749 |
| 24 | M. chitae | ATCC 19627 |
| 25 | M. fortuitum 49403 | ATCC 49403 |
| 26 | M. fortuitum 6841 | ATCC 6841 |
| 27 | M. peregrinum | ATCC 14467 |

Differentiation of TB Complex and MOTT 4 kinds of reference strains (*M. tuberculosis*, *M. bovis*, *M. bovis* BCG, *M. africanum*) which belong to a TB complex of strongly pathogenetic *mycobacteria* could be differentiated from opportunistic pathogens of MOTT by use of specific restriction fragments of 391-bp, 150-bp, and 103-bp. The results are shown in FIGS. 3 and 4.

Figure 3:
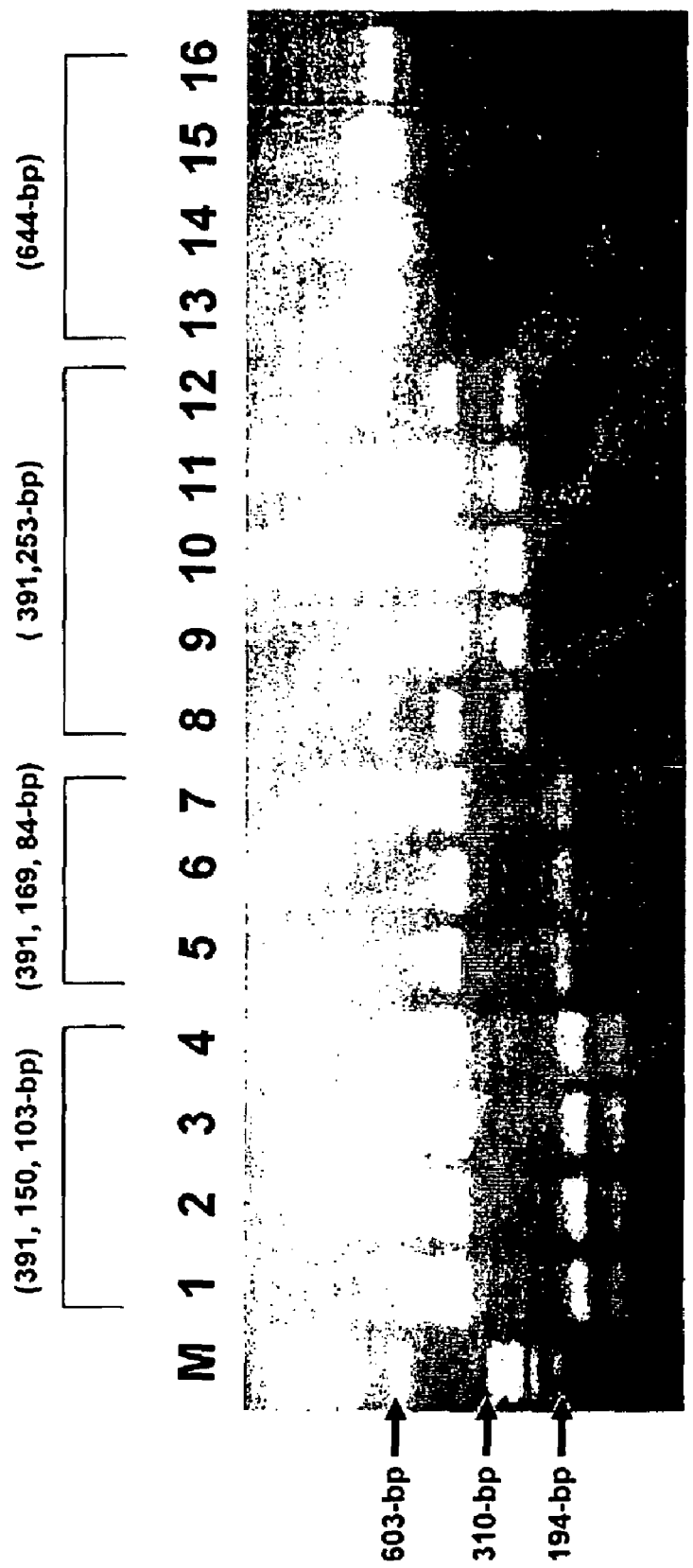
FIG. 3 is a photograph of agarose gel electrophoresis showing the hsp 65 gene fragment of a reference mycobacterial species that was amplified and then treated with Xho I.

FIG. 3 is a photograph of agarose gel electrophoresis of a 644-bp PCR product of an hsp 65 gene fragment of reference strain treated with Xho I.

Lane M: DNA size marker obtained by treating 174 with Hae III,

1: *M. tuberculosis*, 2: *M. bovis*,
3: *M. bovis* BCG, 4: *M. africanum*,
5: *M. avium*, 6: *M. intracellulare*,
7: *M. celatum* Type I, 8: *M. ulcerans*,
9: *M. gordonae*, 10: *M. asiaticum*,
11. *M. marinum*, 12. *M. kansasii*,
13. *M. fortuitum* 6841, 14: *M. abscessus*,
15: *M. chelonae*, 16: *M. peregrinum*

Lanes 1-4 indicated that *M. tuberculosis*, *M. bovis*, *M. bovis* BCG, and *M. africanum* of the TB complex were differentiated from MOTT based on the different restriction fragments.

Differentiation of Fast-growing *Mycobacteria*

Lanes 12-16 in FIG. 3 indicated that 644-bp fast-growing *mycobacteria* including *M. fortuitum* 6841, *M. abscessus*, *M. chelonae*, and *M. peregrinum* were not cleaved by Xho-I, thereby differentiating them from the other *mycobacteria* (FIGS. 3 and 4).

Differentiation of Slow-growing Bacteria Including *M. avium* Complex and *M. kansasii*

It was reported that *M. avium* complex and *M. kansasii* were isolated from a clinical sample at the highest frequency in fast-growing bacteria. As shown in FIG. 3, the *M. avium* complex including *M. avium* (lane 5) and *M. intracellulare* (lane 6) produced three kinds of restriction fragments of 391-bp, 169-bp, and 84-bp by treating with the XhoI, thereby differentiating them from *M. kansasii* (lane 11) producing two kinds of fragments (391-bp and 253-bp). Therefore, the PRA method according to the present invention can differentiate the reference strains with 100% sensitivity and specificity Based on the above results, the differentiation of 27 kinds of reference strains including *M. tuberculosis, M. bovis, M. bovis* BCG, and *M. africanum* of the TB complex, and *M. avium, M. intracellulare*, and *M. kansasii* among MOTT are summarized in FIG. 4.

EXAMPLE 6

Differentiation of Clinically Isolated Strains of *Mycobacteria* by Using the PRA The PCR amplification of EXAMPLE 3 and PRA method of EXAMPLE 5 were performed for 198 clinically-isolated strains shown in Table 4.

TABLE 4

PRA analysis of clinically isolated strains

| strain | No. of isolates |
|---|---|
| TB complex | |
| M. tuberculosis | 54 |
| M. bovis | 9 |
| Slow-growing mycobacteria | |
| M. avium complex | 49 |
| M. kansasii | 30 |
| M. szulgai | 12 |
| M. gordonae | 9 |
| M. marinum | 3 |
| Rapid-growing mycobacteria | |
| M. fortuitum | 17 |
| M. chelonae | 15 |
| Sum | 198 |

Figure 5:
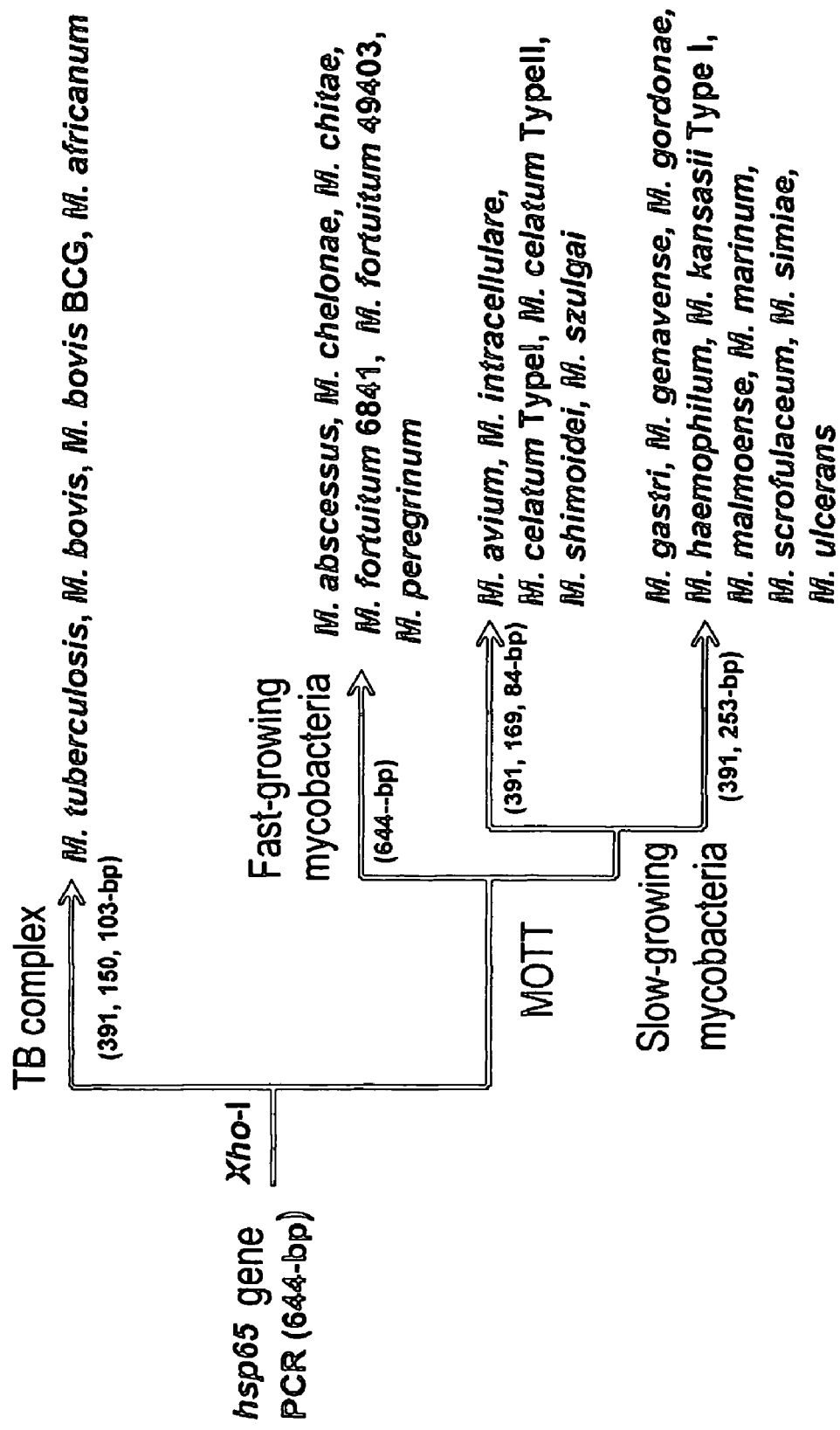
FIG. 5 is a photograph of agarose gel electrophoresis where hsp 65 hsp 65 gene fragments of *mycobacteria* in a clinical sample were amplified and then treated with XhoI.

FIG. 5 is a photograph of 2% agarose gel electrophoresis of a reaction product obtained by treating the amplified hsp 65 gene fragment with Xho I. In panel A, lane M is a DNA size marker obtained by treating 174 with Hae III; Tbc M of Lanes 1-8 and Mac of Lanes 9-16 are concerned with a result of clinical isolates of *M. tuberculosis* and *M. avium* complex, respectively. In panel B, Kac of lanes 1-8 and Foc of lanes 9-16 represent a result of clinical isolates of *M. kansasii* and *M. fortuitum*, respectively.

From FIG. 5, it can be seen that 54 strains of TB complex produced specific restriction fragments of 391 bp, 150 bp, and 103-bp, thereby differentiating them from 144 strains of MOTT. 32 strains of fast-growing *mycobacteria* were not cleaved by the restriction enzyme, so they could be differentiated from the other 168 strains. 49 clinical isolates of *M. avium* complex produced specific restriction fragments of 391 bp, 169 bp, and 84 bp, and thus were differentiated from 39 clinical isolates of a group including *M. kansasii* which produced 2 kinds of restriction fragments (391-pb and 253-bp).

This example confirmed that the PRA method of the present invention by using the hsp 65 gene can be applied to a clinical isolate of *mycobacteria*.

EXAMPLE 7

Identification of Clinical Isolate by Using the Comparative Sequence Analysis

As shown in Table 2, 38 mycobacterial species including 10 kinds of TB complex and 28 MOTT obtained from the Koran Institute of Tuberculosis (Seoul, Korea) were employed as clinically isolated species.

DNA extraction, amplification, and PCR-mediated sequencing of hsp 65 gene fragments were accomplished according to the methods described in Examples 3 and 4. Then, the result was multi-aligned with a sequence database of 54 kinds of reference species in the Megalign program of Dnastar software according to the method of Example 4, to infer a phylogenetic tree according to the Neighbor-Joining method of Mega software. The identification result showed that 38 clinically isolated strains were identified to species level with 100% sensitivity and specificity as indicated in Table 2 and FIGS. 7a to 7d. The result in FIGS. 7a to 7d are specifically described:

FIG. 7a: Identification of 4 strains of *M. gordonae* (KIT 32101, 32104, 32105, 32106), 4 strains of *M. szulgai* (KIT 31102, 31103, 31106, 31107), and a strain of *M. marinum* (KIT 21101).

Figure 7B:
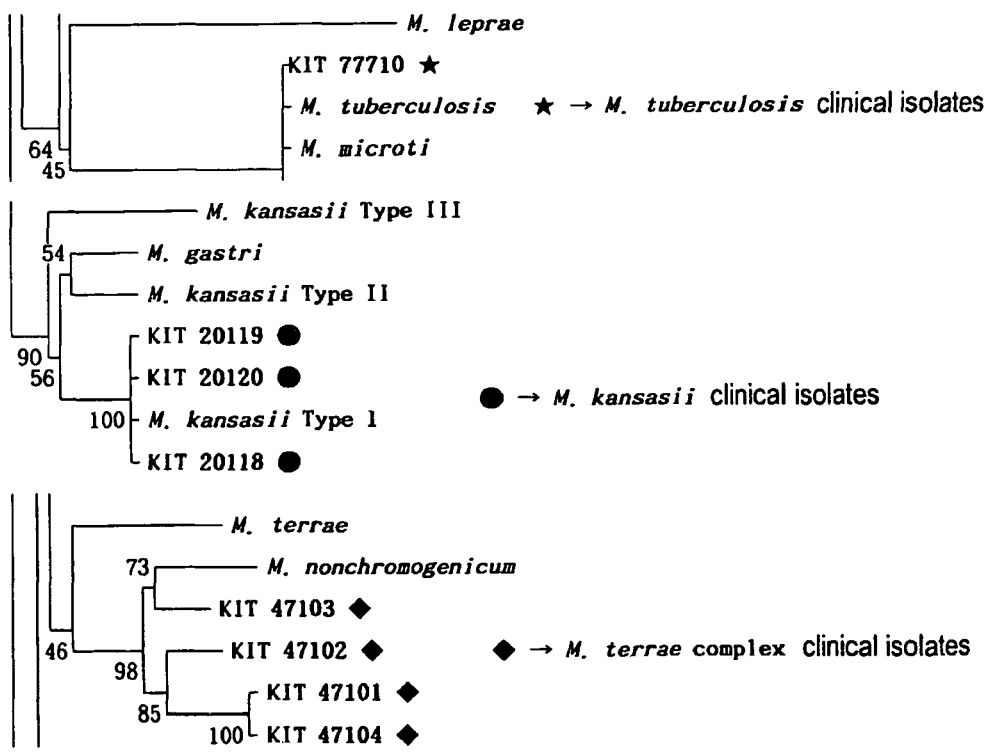

FIG. 7b: Identification of 2 strains of *M. scrofulaceum* (KIT 30101, 30102), and 4 strains of *M. avium* complex (KIT 41105, 41110, 41111, 41115).

Figure 7C:
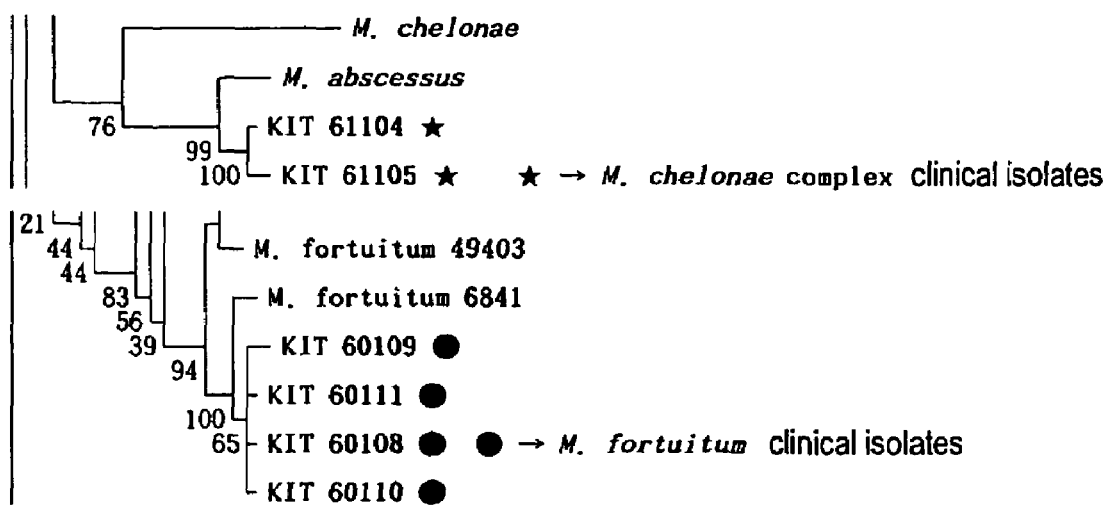

FIG. 7c: Identification of 1 strain of *M. tuberculosis* (KIT 77710), 3 strains of *M. kansasii* (KIT 20118, 20119, 20120), and 4 strains of *M. terrae* complex (KIT 47101, 47102, 47103, 47104).

Figure 7D:
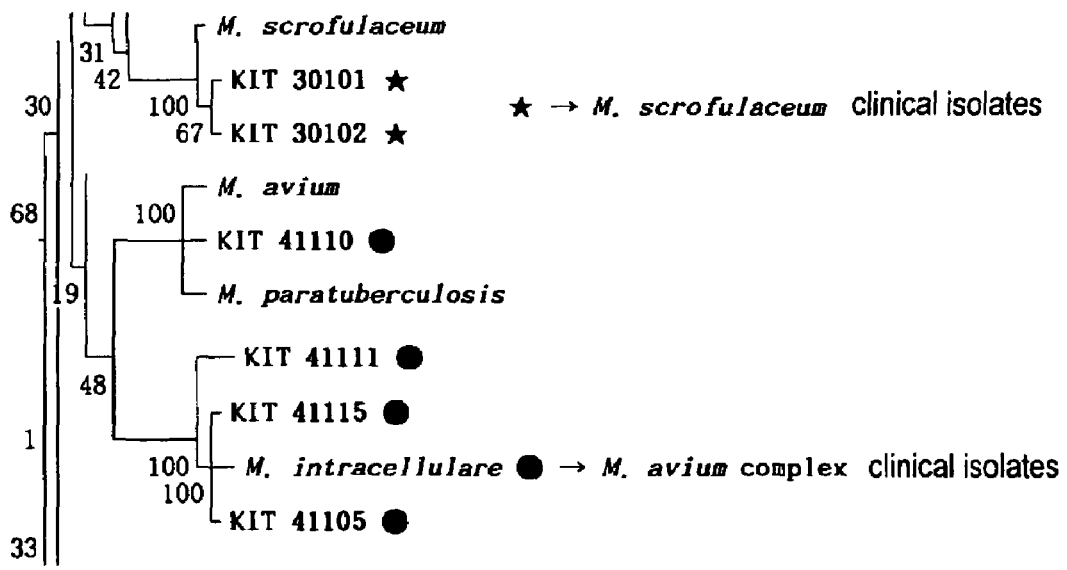

FIG. 7d: Identification of 2 strains of *M. chelonae* complex (KIT 61104, 61105), and 4 strains of *M. fortuitum* (KIT 60108, 60109, 60110, 60111).

a) 10 strains of *M. tuberculosis* were identified as *M. tuberculosis* (Table 2 and FIG. 7b). The clinically isolated strains had 100% nucleotide sequence homology with *M. tuberculosis* ATCC 27284.

b) 3 strains of *M. avium* complex were identified as *M. intracellulare* and a strain of *M. avium* complex was identified as *M. avium*, respectively. *M. avium* (KIT 41110) had 99.5% nucleotide sequence homology with *M. avium* ATCC 25281 which included 3 different nucleotides in a 604-bp hsp 65 gene fragment. When the nucleotide sequences of 3 strains of *M. intracellulare* (KIT 41105, 41111, and 51115) were compared with that of *M. Intracellulare* ATCC 13850, they showed 99.0-99.8% sequence homology.

c) 2 strains of *M. scrofulaceum* (KIT 30101, 30102) were identified as *M. scrofulaceum* (FIG. 7b). 2 clinically isolated strains and *M. scrofulaceum* ATCC 19981 had 99.8-100% nucleotide sequence homology.

d) 3 strains of *M. kansasii* (KIT 20118, 20119, 20120) had 100% nucleotide sequence homology, and were identified as *M. kansasii* Type I ATCC 12478 (FIG. 7c). The result is consistent with that of the biochemical identification method.

e) 4 strains (KIT 32101, 32104, 32105, and 32106) were identified as *M. gordonae* (FIG. 7a and Table 2). When comparing the nucleotide sequences of a 604-bp hsp 65 gene fragment of 4 clinically isolated strains, they had 99.2-99.8% sequence homology with each other, but they had 95.9-96.3% sequence homology with *M. gordonae* ATCC 14470. The result indicates a considerably low sequence homology between *M. gordonae* species.

Like the results of the biochemical identification method, 4 clinically isolated strains (KIT 31102, 31103, 31106, 31107) were identified as *M. szulgai* (FIG. 7a, and Table 2), and had 99.5-100% sequence homology with their reference strain (*M. szulgai* ATCC 35799)

Like the results of the biochemical identification method, a clinically isolated strain was identified as *M. marinum* (FIG. 7a and Table 2), and had 99.3% sequence homology with its reference strain (*M. marinum* ATCC 927). 4 strains were identified as M. nonchromogenicum of *M. terrae* complex, and had 95.0-100% sequence homology with *M. nonchromogenicum* ATCC 19530. The result is consistent with the previous report that *M. terrae* complex had sequence heterogeneity.

f) Like the biochemical identification method, 2 clinically isolated strains (KIT 61104, 61105) were identified as *M. abscessus* of *M. chelonae* complex. The identification method of the present invention resolves the problem of the conventional biochemical method in which *M. chelonae* and *M. abscessus* cannot be differentiated. The strains have 98.4-99.5% nucleotide sequence homology with *M. abscessus* CAP97E-03.

Like the biochemical identification method, 4 clinically isolated strains were identified as *M. fortuitum* ATCC 6841, and had 99.4-100% sequence homology with the reference strain. In the present invention, *M. fortuitum* ATCC 6841, *M. fortuitum* ATCC 49403, *M. fortuitum* ATCC 49404, and *M. peregrinum* were employed as reference strains for *M. fortuitum*.

What is claimed is:

1. A polynucleotide of an hsp 65 gene fragment of mycobacterial species, wherein the fragment is amplified by using a pair of primers for amplifying the hsp 65 gene fragment of mycobacterial species, one primer consists of the nucleotide sequence of SEQ ID NO: 55 and the other primer consists of the nucleotide sequence of SEQ ID NO: 56; and the size of the amplified hsp 65 gene fragment is 604 bp excluding the primers.

2. A polynucleotide selected from the group of polynucleotides consisting of SEQ ID NOs: 1-5, 8-11, 13-38, 40-44, 46-54, and polynucleotides complementary thereto.

3. A polynucleotide set for the detection or identification of mycobacterial species wherein the set consists of at least two hsp 65 gene fragments selected from the group of polynucleotides consisting of SEQ ID NOs: 1-5, 8-11, 13-38, 40-44, 46-54, and polynucleotides complementary thereto.

4. A method for the identification of a mycobacterial species comprising the steps of:

(1) amplifying an hsp 65 gene fragment of a mycobacterial species of interest with primers for amplifying an hsp65 gene of *mycobacteria*; and (2) hybridizing the amplified hsp65 gene fragment with a probe set consisting of at least a probe selected from the group of polynucleotides consisting of SEQ ID NOs: 1-5, 8-11, 13-38, 40-44, 46-54, and polynucleotides complementary thereto.

5. A pair of primers for amplifying an hsp 65 (Heat Shock Protein 65) gene fragment of mycobacterial species, wherein one primer consists of the nucleotide sequence of SEQ ID NO: 55 and the other primer consists of the nucleotide sequence of SEQ ID NO: 56, and the size of the amplified hsp 65 gene fragment is 604 bp excluding the primers.

6. A kit for the differentiation or diagnosis of TB complex and MOTT comprising a pair of primers of claim 5 and Xho I, wherein the mycobacterial species is differentiated or diagnosed based on the size of restriction fragment(s) which is obtained by amplifying an hsp 65 gene fragment of mycobacterial species in a sample with the primers to produce an amplified fragment and analyzing the amplified fragment according to an RFLP analysis method.

7. A method for the identification of mycobacterial species comprising the steps of:
  (1) amplifying an hsp 65 gene fragment of mycobacterial species with primers of claim 5, wherein the size of the amplified hsp 65 gene fragment is 644 bp including the primers; and
  (2) analyzing the amplified fragment according to the RFLP (Restriction Fragment Length Polymorphism) analysis method using a restriction enzyme recognition site in the amplified fragment.

8. The method of claim 7, wherein the restriction enzyme is Xho I.

9. The method of claim 8 comprising the step of treating the amplified hsp 65 gene fragment with Xho I to produce restriction fragment(s), and analyzing the restriction fragment(s) according to an RFLP analysis method to differentiate TB complex (*Mycobacterium tuberculosis* complex) and MOTT (*Mycobacteria* other than *Mycobacterium tuberculosis*).

10. The method of claim 9, wherein the restriction fragments are 391-bp, 150-bp, and 103-bp fragments to identify the TB complex.

11. The method of claim 9, wherein the 644-bp hsp 65 gene fragment is not cleaved by a restriction enzyme to identify fast-growing *mycobacteria* of MOTT.

12. The method of claim 9, wherein the restriction fragments are 391-bp, 169-bp, and 48-bp to identify a mycobacterial species selected from the group consisting of *M avium, M intracellulare, M celatum, M shimoidei*, and *M szulgai*.

13. The method of claim 9, wherein the restriction fragments are 391-bp and 253-bp to identify a mycobacterial species selected from the group consisting of *M gastri, M genavense, M gordonae, M haemophilum, M kansasii, M mahnoense, M marinum, M scrofulaceum, M simiae*, and *M ulcerans*.

* * * * *

UNITED STATES PATENT AND TRADEMARK OFFICE
CERTIFICATE OF CORRECTION

PATENT NO. : 7,732,589 B2
APPLICATION NO. : 10/500586
DATED : June 8, 2010
INVENTOR(S) : Kim et al.

It is certified that error appears in the above-identified patent and that said Letters Patent is hereby corrected as shown below:

Column 1,

Line 11, "filed of Jan. 21, 2003" should read --filed on Jan. 21, 2003--;

Line 57, "cause" should read --causes--.

Column 4,

Line 50, "5'-ATCGCCMGGAGATCGAGCT-3'" should read --5'-ATCGCCAAGGAGATCGAGCT-3'--;

Line 52, "5'-MGGTGCCGCGGATCTTGTT-3'" should read --5'-AAGGTGCCGCGGATCTTGTT-3'--.

Column 14,

Lines 9 and 10, "100 A phenol:chloroform:isopropylalcohol" should read --100 $^{u\ell}$ phenol:chloroform:isopropylalcohol--;

Line 31, "623-bp" should read --1623-bp--.

Column 16,

Line 15, cancel "is".

Column 64,

Line 14, "*M mahnoense*" should read --*M. malmoense*--.

Signed and Sealed this
Twenty-fifth Day of January, 2011

David J. Kappos
*Director of the United States Patent and Trademark Office*

SEQUENCE LISTING

```
<160> NUMBER OF SEQ ID NOS: 56

<210> SEQ ID NO 1
<211> LENGTH: 604
<212> TYPE: DNA
<213> ORGANISM: Mycobacterium abscessus

<400> SEQUENCE: 1
ggaggacccg tacgagaaga tcggcgctga gctggtcaag gaagttgcca agaagaccga      60
cgacgtcgcg ggtgacggca ccaccaccgc caccgtgctc gcccaggctc tggtcaagga     120
aggtctgcgt aacgtcgccg ccggcgccaa cccgctcggc ctgaagcgcg gtatcgagaa     180
```

-continued

```
ggccgtcgag aaggtcaccg agacgctgct gaagagcgcc aaggaggtcg agaccaagga      240
gcagatcgcg gccacggccg gtatctccgc gggcgaccag tccatcggcg acctgatcgc      300
cgaggccatg gacaaggttg gtaacgaggg tgtcatcacc gtcgaggagt ccaacacctt      360
cggcctgcag ctggagctca ccgagggtat gcgcttcgac aagggctaca tctcgggcta      420
cttcgtgacc gacgccgagc gtcaggaagc cgtcctggag gatccctaca tcctgctggt      480
cagctccaag gtgtcgaccg tcaaggatct gcttccgttg ctggagaagg tcattcaggc      540
cggcaagccg ctgctgatca tcgccgagga cgtcgagggc gaggctctct ccactctggt      600
cgtc                                                                  604

<210> SEQ ID NO 2
<211> LENGTH: 604
<212> TYPE: DNA
<213> ORGANISM: Mycobacterium africanum

<400> SEQUENCE: 2
ggaggatccg tacgagaaga tcgg

<210> SEQ ID NO 4
<211> LENGTH: 604
<212> TYPE: DNA
<213> ORGANISM: Mycobacterium aichiense

<400> SEQUENCE: 4

```
cgaggacccg tacgagaaga tcggcgctga gctggtcaag gaagtcgcca agaagactga      60
cgatgtcgcg ggcgacggca ccaccaccgc caccgtgctc gctcaggctc tggttcgcga     120
aggtctgcgc aacgtcgctg ccggcgccaa cccgctcggc ctgaagcgcg gcatcgagaa     180
ggccgtcgag aagatcaccg agacgctcct caagagcgcc aaggaggtcg agaccaagga     240
ccagatcgcg gccaccgccg gatctccgc gggcgaccag accatcggtg acctgatcgc      300
cgaggccatg gacaaggtcg gcaacgaggg tgtcatcacc gtcgaggagt cgaacacctt     360
cggcctgcag ctcgagctca ccgagggtat gcgcttcgac aagggctaca tctcgggtta     420
cttcgtgacc gacgccgagc gtcaggaagc ggtcctcgag gatccgtaca tcctgctggt     480
gtcgtcgaag gtctcgaccg tcaaggacct gcttcccttg ctggagaagg tcattcagtc     540
gggcaagccg ctgctgatca tcgccgagga cgtcgagggc gaagccctgt ccaccctggt     600
ggtc                                                                  604
```

<210> SEQ ID NO 5
<211> LENGTH: 604
<212> TYPE: DNA
<213> ORGANISM: Mycobacterium avium

<400> SEQUENCE: 5

```
ggaggacccg tacgagaaga tcggcgccga gctggtcaag gaagtcgcca agaagaccga      60
cgacgtcgcc ggtgacggca cgacgacggc cacggtgctc gcccaggcgt tggtccgcga     120
gggcctgcgc aacgtcgcgg ccggcgccaa cccgctgggt ctcaagcgcg gcatcgagaa     180
ggccgtcgag aaggtcaccg agaccctgct caagtcggcc aaggaggtcg agaccaagga     240
ccagatcgct gccaccgcgg ccatctccgc gggcgaccag tcgatcggcg acctgatcgc      300
cgaggcgatg gacaaggtcg gcaacgaggg cgtcatcacc gtcgaggagt ccaacacctt     360
cggcctgcag ctcgagctca ccgagggtat gcggttcgac aagggttaca tctcgggcta     420
cttcgtcacc gacgccgagc gtcaggaagc cgtcctcgag gatccgttca tcctgctggt     480
cagctccaag gtctcgaccg tcaaggacct gctgccgctg ctggagaagg tcatccaggc     540
cggcaagccg ctgctgatca tcgccgagga cgtcgagggc gaggccctgt ccaccctggt     600
cgtc                                                                  604
```

<210> SEQ ID NO 6
<211> LENGTH: 604
<212> TYPE: DNA
<213> ORGANISM: Mycobacterium bovis

<400> SEQUENCE: 6

```
ggaggatccg tacgagaaga tcggcgccga gctggtcaaa gaggtagcca agaagaccga      60
tgac -continued

| cttcgtgacc gacccggagc gtcaggaggc ggtcctggag gacccctaca tcctgctggt | 480 |
| cagctccaag gtgtccactg tcaaggatct gctgccgctg ctcgagaagg tcatcggagc | 540 |
| cggtaagccg ctgctgatca tcgccgagga cgtcgagggc gaggcgctgt ccaccctggt | 600 |
| cgtc | 604 |

<210> SEQ ID NO 7
<211> LENGTH: 604
<212> TYPE: DNA
<213> ORGANISM: Mycobaterium bovis BCG

<400> SEQUENCE: 7

| ggaggatccg tacgagaaga tcggcgccga gctggtcaaa gaggtagcca agaagaccga | 60 |
| tgacgtcgcc ggtgacggca ccacgacggc caccgtgctg gcccaggcgt tggttcgcga | 120 |
| gggcctgcgc aacgtcgcgg ccggcgccaa cccgctcggt ctcaaacgcg gcatcgaaaa | 180 |
| ggccgtggag aaggtcaccg agaccctgct caagggcgcc aaggaggtcg agaccaagga | 240 |
| gcagattgcg gccaccgcag cgatttcggc gggtgaccag tccatcggtg acctgatcgc | 300 |
| cgaggcgatg gacaaggtgg gcaacgaggg cgtcatcacc gtcgaggagt ccaacacctt | 360 |
| tgggctgcag ctcgagctca ccgagggtat gcggttcgac aagggctaca tctcggggta | 420 |
| cttcgtgacc gacccggagc gtcaggaggc ggtcctggag gacccctaca tcctgctggt | 480 |
| cagctccaag gtgtccactg tcaaggatct gctgccgctg ctcgagaagg tcatcggagc | 540 |
| cggtaagccg ctgctgatca tcgccgagga cgtcgagggc gaggcgctgt ccaccctggt | 600 |
| cgtc | 604 |

<210> SEQ ID NO 8
<211> LENGTH: 604
<212> TYPE: DNA
<213> ORGANISM: Mycobacterim celatum Type 1

<400> SEQUENCE: 8

| ggaggacccc tacgaaaaga tcggcgccga gctggtcaag gaagtcgcca agaagaccga | 60 |
| cgacgtcgcg ggtgacggta cgacgacggc cacggtgctg gcccaggcgc tggtcaagga | 120 |
| gggcctgcgc aacgtcgccg ccggcgccaa cccgctcggc ctgaagcgcg gcatcgagaa | 180 |
| ggccgtcgag aaggtcaccg agacgctgct caagggcgcc aaggaggtcg agaccaagga | 240 |
| gcagattgct gccaccgcgg ccatctccgc cggcgaccag tcgatcggcg acctgatcgc | 300 |
| cgaggccatg gacaaggtcg gcaacgaggg cgtcatcacc gtcgaggagt ccaacacctt | 360 |
| cggcctgcag ctcgagctca ccgagggtat gcgcttcgac aagggctaca tctcgggtta | 420 |
| cttcgtcacc gacgccgagc gtcaggaggc ggtgctcgag gagccgtaca tcctgctggt | 480 |
| cagctccaag gtgtcgacgg tcaaggacct gcttccgctg ctggagaagg tcatccaggc | 540 |
| cggcaagccg ctgctgatca tcgccgagga cgtcgagggc gaagccctct ccaccctggt | 600 |
| cgtc | 604 |

<210> SEQ ID NO 9
<211> LENGTH: 604
<212> TYPE: DNA
<213> ORGANISM: Mycobaterium celatum TypeII

<400> SEQUENCE: 9

| ggaggacccc tacgagaaga tcggcgccga gctggtcaag gaagtcgcca agaagaccga | 60 |
| cgacgtcgcg ggtgacggta cgacgacggc caccgtgctg gcccaggcgc tggtcaagga | 120 |

```
aggcctgcgc aacgtcgccg ccggtgccaa cccgctcggc ctgaagcgcg gtatcgagaa    180
ggccgtcgag aaggtcaccg agacgctgct caagggcgcc aaggaggtcg agaccaagga    240
gcagatcgct gccaccgcgg ccatctccgc cggtgaccag tcgatcggcg acctgatcgc    300
cgaggcgatg gacaaggtcg gcaacgaggg cgtcatcacc gtcgaggagt ccaacacctt    360
cggcctgcag ctcgagctca ccgagggtat gcgcttcgac aagggctaca tctcgggtta    420
cttcgtcacc gacgccgagc gtcaggaggc ggtgctcgag gagccctaca tcctgctggt    480
cagctccaag gtgtcgacgg tcaaggatct gctgccgctg ctggagaagg tcatccaggc    540
cggcaagccg ctgctgatca tcgccgagga cgtcgagggt gaggcgttga gcaccctggt    600
cgtc                                                                604
```

```
<210> SEQ ID NO 10
<211> LENGTH: 604
<212> TYPE: DNA
<213> ORGANISM: Mycobacterium chelonae

<400> SEQUENCE: 10
ggaggacccg tacgagaaga tcggcgctga gctggtcaag gaagttgcca agaagactga     60
cgacgtcgcg ggtgacggca ctactaccgc caccgtgctt gcccaggctc tggtcaagga    120
aggtctgcgt aacgtcgctg ccggcgccaa cccgctcggc ctgaagcgcg gcatcgagaa    180
ggccgtggag gccgtcacca gctctctgct ggactccgcc aaggagatcg acaccaagga    240
gcagatcgcg gccaccgcgg gcatctccgc gggtgaccag tccatcggtg atctgatcgc    300
cgaggccatg gacaaggtcg gcaacgaggg tgtcatcacc gtcgaggagt ccaacacctt    360
cggcctgcag ctggagctca ccgagggcat gcgcttcgac aagggctaca tctcgggtta    420
cttcgtgacc gacgccgagc gtcaggaagc cgtcctggag gatccctaca tcctgctggt    480
cagctccaag gtctcgaccg tcaaggacct acttcccttg ctggagaagg tcatccaggg    540
cggcaagccg ctgctgatca tcgccgagga cgttgagggc gaggctctct cgaccctggt    600
cgtc                                                                604
```

```
<210> SEQ ID NO 11
<211> LENGTH: 604
<212> TYPE: DNA
<213> ORGANISM: Mycobacterium chitae

<400> SEQUENCE: 11
ggaggacccg tacgagaaga tcggcgccga gctggtcaag gaagtcgcca agaagactga     60
cgacgtcgcc ggcgacggca ccaccaccgc caccgttctg gccaggcgc tggttcgcga    120 aggtctgcgc aacgtcgcgg ccggcgccaa cccgctcggc ctgaagcgcg gcatcgagaa    180
ggccgtcgag accgtctcgg agaacctgct caagtcggcc aaggaggtcg agaccaagga    240
gcagatcgcc gccaccgccg gatctccgc gggcgacacc accatcggtg acctgatcgc    300
cgaggccatg gacaaggtgg gcaacgaggg tgtcatcacc gtcgaggagt ccaacacctt    360
cggcctgcag ctggagctca ccgagggcat gcgcttcgac aagggctaca tctcgggcta    420
cttcgtgacc gacgccgagc gtcaggaagc cgtcctggag gatccctaca tcctgctggt    480
cagctcgaag atctcgaccg tcaaggacct gctgccgctg ctggagaagg tcatccagtc    540
cggcaagccg ctgctgatca tcgccgagga cgtcgagggc gaggccctgt cgaccctggt    600
ggtc                                                                604
```

<210> SEQ ID NO 12
<211> LENGTH: 604
<212> TYPE: DNA
<213> ORGANISM: Mycobacterium microti

<400> SEQUENCE: 12

```
ggaggatccg tacgagaaga tcggcgccga gctggtcaaa gaggtagcca agaagaccga    60
tgacgtcgcc ggtgacggca ccacgacggc caccgtgctg gcccaggcgt tggttcgcga   120
gggcctgcgc aacgtcgcgg ccggcgccaa cccgctcggt ctcaaacgcg gcatcgaaaa   180
ggccgtggag aaggtcaccg agaccctgct caagggcgcc aaggaggtcg agaccaagga   240
gcagattgcg gccaccgcag cgatttcggc gggtgaccag tccatcggtg acctgatcgc   300
cgaggcgatg gacaaggtgg gcaacgaggg cgtcatcacc gtcgaggagt ccaacacctt   360
tgggctgcag ctcgagctca ccgagggtat gcggttcgac aagggctaca tctcggggta   420
cttcgtgacc gacccggagc gtcaggaggc ggtcctggag gacccctaca tcctgctggt   480
cagctccaag gtgtccactg tcaaggatct gctgccgctg ctcgagaagg tcatcggagc   540
cggtaagccg ctgctgatca tcgccgagga cgtcgagggc gaggcgctgt ccaccctggt   600
cgtc                                                                604
```

<210> SEQ ID NO 13
<211> LENGTH: 604
<212> TYPE: DNA
<213> ORGANISM: Mycobaterium flavescens

<400> SEQUENCE: 13

```
ggaggacccg tacgagaaga tcggcgctga gctggtcaag gaagtcgcca agaagaccga    60
cgacgtcgcg ggcgacggca ccaccaccgc caccgtgctg gcccaggcgc tcgtgcgcga   120
gggtctgcgc aacgtcgcgg ccggcgccaa cccgatggcg ctgaagcgcg gtatcgagaa   180
ggccgtcgag aaggtcaccg agacgctgct gaagtcggcc aaggaggtcg agaccaagga   240
gcagatcgct gccaccgccg cgatctcggc gggcgacacc cagatcggca agctgatcgc   300
cgaggccatg gacaaggtcg gcaacgaggg tgtcatcacc gttgaggagt ccaacacctt   360
cgggctgcag ctcgagctca ccgagggtat gcgcttcgac aagggctaca tctcgggtta   420
cttcgtgacc gacgccgagc gtcaggaagc ggtcctcgag gatccctgca tcctgctcgt   480
gtcgtccaag gtgtcgaccg tcaaggatct gctcccgttg ctggagaagg tcattcaggc   540
cggcaagccg gtgctgatca tcgccgagga cgtcgagggt gaggccctgt cgaccctggt   600
ggtc                                                                604
```

<210> SEQ ID NO 14
<211> LENGTH: 604
<212> TYPE: DNA
<213> ORGANISM: Mycobaterium fortuitum 6841

<400> SEQUENCE: 14

```
ggaggacccg tacgagaaga tcggcgctga gctcgtcaaa gaggtcgcca agaagaccga    60
cgacgtcgcg ggcgacggca ccaccaccgc caccgttctg gcacaggccc tggttcgtga   120
aggtctgcgc aacgtcgctg ccggcgccaa cccgctcggc ctgaagcgcg gcatcgagaa   180
ggccgtcgag aaggtcaccg agacgctgct gaagagcgcc aaggaggtgg agaccaagga   240
gcagatcgct gccaccgccg gtatctccgc cggtgaccag tccatcggtg acctgatcgc   300
cgaggccatg gacaaggtcg gcaacgaggg tgtcatcacc gtcgaggaga gcaacacctt   360
```

```
cggcctgcag ctggagctca ccgggggtat gcgcttcgac aagggctaca tctcgggcta    420
cttcgtgacc gacgccgagc gtcaggaagc cgtcctggag atccctaca tcctgctggt     480 cagctccaag gtctcgaccg tcaaggacct gctgccgctg ctggagaagg tcatccagtc    540
cggcaagccg ctgctgatca tcgccgagga cgtcgagggc aagccctgt cgaccctggc     600 ggtc                                                                 604

<210> SEQ ID NO 15
<211> LENGTH: 604
<212> TYPE: DNA
<213> ORGANISM: Mycobacterium fortuitum 49403

<400> SEQUENCE: 15
ggaggacccg tacgagaaga tcggcgctga gctcgtcaaa gaggtcgcca agaagaccga    60
cgacgtcgcg ggcgacggca ccaccaccgc caccgttctg gcccaggccc tggttcgcga   120
aggtctgcgc aacgtcgctg ccggcgccaa cccgctcggc ctgaagcgcg gcatcgagaa   180
ggccgtcgag aaggtcaccg agacgctgct gaagagcgcc aaggaggtgg agaccaagga   240
gcagatcgct gccaccgccg gtatctccgc cggtgaccag tccatcggtg acctgatcgc   300
cgaggccatg gacaaggtcg gcaacgaggg tgtcatcacc gtcgaggaga gcaacacctt   360
cggcctgcag ctggagctca ccgagggtat gcgcttcgac aagggctaca tctcgggtta   420
cttcgtgacc gacgccgagc gtcaggaagc cgtcctggag atccctaca tcctgctggt    480 cagctccaag gtctcgaccg tcaaggacct gctgccgctg ctggagaagg tcatccagtc   540
cggcaagccg ctgctgatca tcgccgagga cgtcgagggc aagccctgt ccaccctggt    600 ggtc                                                                 604

<210> SEQ ID NO 16
<211> LENGTH: 604
<212> TYPE: DNA
<213> ORGANISM: Mycobacterium fortuitum 49404

<400> SEQUENCE: 16
ggaggacccg tacgagaaga tcggcgcaga gctggtcaag gaagtcgcca agaagactga    60
cgacgtcgca ggcgacggca ccaccacggc caccgtgctc gcccaggctc tggttcgcga   120
aggtctgcgc aacgtcgcag ccggcgccaa cccgctcggc ctgaagcgcg gcatcgagaa   180
ggctgtcggg gccgtcaccc agacgctgct gaagtccgcc aaggaggtgg agaccaagga   240
gcagatcgct gccaccgccg cgatctccgc cggtgacgtc cagatcggcg agctcatcgc   300
cgaggccatg gacaaggtcg gcaacgaggg tgtcatcacc gtcgaggagt cgaacacctt   360
cggcctgcag ctggagctca ccgagggtat gcgcttcgac aagggctaca tctcgggtta   420
cttcgtgacc gacgccgagc gtcaggaagc ggtcctcgag atccgtaca tcctgctcgt    480 ctcgtcgaag gtctcgacgg tcaaggacct gctgccctg ctggagaagg tcatccaggc    540
cggcaagccg ctgctgatca tcgccgagga cgtcgagggc aagccctgt ccaccctggt    600 ggtc                                                                 604

<210> SEQ ID NO 17
<211> LENGTH: 604
<212> TYPE: DNA
<213> ORGANISM: Mycobacterium gastri

<400> SEQUENCE: 17
```

```
ggaggacccg tacgagaaga tcggcgccga gctggtcaag gaagtcgcca agaagaccga    60
cgacgtcgcc ggcgacggca ccaccacggc caccgtgctc gcgcaggcgc tggtcaagga   120
gggcctgcgc aacgtcgcgg ccggcgccaa cccgctgggc ctgaagcgcg gcatcgagaa   180
ggccgtcgag aaggtcaccg agacgctgct caagggcgcc aaggaggtcg agaccaagga   240
gcagatcgcg gccaccgcgg ccatctccgc cggtgaccag tcgatcggcg acctgatcgc   300
cgaggcgatg gacaaggtgg gcaacgaggg tgtcatcacc gtcgaggagt ccaacacctt   360
cggcctgcag ctcgagctca ccgagggcat gcggttcgac aagggctaca tctccggcta   420
cttcgtcacc gacgctgagc gtcaggaagc tgttctggag daccctaca tcctgctggt    480 cagctcgaag gtctcgaccg tcaaggacct gctgccgctg ttggagaagg tcatccaggc   540
gggcaagccg ctgctgatca tcgccgagga cgtcgagggc gaggcgctgt ccaccctggt   600
cgtc                                                                604

<210> SEQ ID NO 18
<211> LENGTH: 604
<212> TYPE: DNA
<213> ORGANISM: Mycobacterium genavense

<400> SEQUENCE: 18 ggaggaccccc tacgagaaga tcggcgctga gctggtcaag gaagtcgcca agaagaccga    60
cgacgtcgcc ggtgacggca ccgacggc caccgtgctc gctcaggcgc tcgtcaagga     120
gggcctgcgc aacgtggcgg ccggcgccaa cccgctgggc ctcaagcgcg gcatcgagaa   180
ggccgtcgaa aaggtcaccg agacgctgct gaagtcggcc aaggatgtcg agaccaagga   240
ccagatcgct gccaccgccg cgatttccgc gggcgaccag tcgatcggcg acctgatcgc   300
cgaggcgatg gacaaggtcg gcaacgaggg cgtcatcacc gtcgaggagt ccaacacctt   360
cgggctgcag ctcgagctca ccgagggtat gcgcttcgac aagggctaca tctcgggcta   420
cttcgtcacc gacgccgagc gtcaggaagc cgtcctggag gacccgttca tcctgctggt   480
cagctccaag gtgtcgacgg tcaaggacct gctgccgctg ctggagaagg tcatccaggc   540
cggcaagccg ctgctgatca tcgccgagga cgtcgagggc gaggcgctga gcaccctggt   600
cgtc                                                                604

<210> SEQ ID NO 19
<211> LENGTH: 603
<212> TYPE: DNA
<213> ORGANISM: Mycobacterium gordonae

<400> SEQUENCE: 19
gaggacccgt acgagaagat cggcgctgag ctggtcaagg aagtcgccaa gaagaccgac    60
gacgttgccg gcgacggcac gacgacggcg accgtgctgg cgcaggcact ggtcaaggaa   120
ggcctgcgca acgtagccgc cggcgccaac ccgctggggc tgaagcgcgg catcgagaag   180
gccgtggaga aggtcaccca gaccctgctc agctcggcca aggacgtcga gaccaaggag   240
cagatcgcgc ccaccgcggg catctccgcg ggtgaccagt cgatcggtga cctgatcgcc   300
gaggcgatgg acaaggtcgg caacgagggc gtcatcaccg tcgaggagtc caacaccttc   360
ggcctgcagc tcgagctgac cgagggcatg cggttcgaca agggctacat ctcgggctac   420
ttcgtcaccg acgccgagcg tcaggaagcc gtcctggaag accccctacat cctgctggtg   480 tccagcaagg tgtcgaccgt gaaggacctg ctgccgctgc tggagaaggt cattcagggt   540
ggcaagccgc tgctgatcat cgccgaggac gtcgagggcg aagcgctgtc gaccctggtc   600
```

```
gtc                                                                603

<210> SEQ ID NO 20
<211> LENGTH: 604
<212> TYPE: DNA
<213> ORGANISM: Mycobacterium haemophilum

<400> SEQUENCE: 20
ggaggacccg tacgagaaga tcggcgccga gctggtcaag gaagtcgcca agaagaccga      60
cgacgtcgct ggtgatggca ccacgacggc gacggtgctg gctcaggcgc tggtcaaaga     120
gggcctgcgt aacgtcgcgg ccggcgccaa cccgctgggt ctcaagcgcg gcatcgagaa     180
ggcggtcgag aagatcaccg agacgctgct caagggcgcc aaggaggtcg agaccaagga     240
ccaaattgcg gccaccgcag cgatctcggc gggtgaccag tcgatcggcg acctgatcgc     300
cgaggcgatg gacaaggtcg gcaacgaggg cgtcatcacc gtcgaggagt ccaacacctt     360
cggcctgcag ctcgagctca ccgagggcat gcggttcgat aagggctaca tctcgggcta     420
cttcgtcacc gacgccgagc gccaggaagc cgtcctggag acccctaca  tcctgctggt     480 cagctccaag gtgtcgaccg tcaaggacct gctgccactg ttggagaagg tcatccaggc     540
cggcaagccg ctgctgatca tcgccgagga cgtcgagggc gaggcgctgt ccaccctggt     600
cgtc                                                               604

<210> SEQ ID NO 21
<211> LENGTH: 603
<212> TYPE: DNA
<213> ORGANISM: Mycobacterium interjectum

<400> SEQUENCE: 21
gaggacccgt acgagaagat cggcgccgag ctggtcaagg aagtcgccaa gaagaccgac      60
gacgtcgccg gtgacggcac gacgacggcc acggtgctgg cccaggccct ggtcaaggag     120
ggcctgcgca acgtcgcggc cggcgccaac ccgccggcgc tcaagcgcgg catcgaaaag     180
gccgtcgaga aggtcaccga gaccctgctg aagtcggcca aggatgtcga gaccaaggag     240
cagatcgccg cgaccgccgc gatctccgcg ggcgaccagt cgatcggcga cctcatcgcc     300
gaggcgatgg acaaggtcgg caacgagggc gtcatcaccg tcgaggagtc caacaccttc     360
ggcctgcagc tcgagctcac cgagggcatg cggttcgaca agggctacat ctcgggctac     420
ttcgtcaccg acgccgagcg tcaggaagcg gtcctcgagg acccctacat cctgctggtc     480
agctcgaagg tgtcgacggt caaggacctg ttgccgctgc tggagaaggt catccaggcc     540
ggcgagccgc tgttgatcat cgccgaggac gtcgagggcg aggcgctgtc caccctggtc     600
gtc                                                                603

<210> SEQ ID NO 22
<211> LENGTH: 604
<212> TYPE: DNA
<213> ORGANISM: Mycobacterium intermedium

<400> SEQUENCE: 22
ggaggacccg tacgagaaga tcggcgccga gctggtcaag gaagttgcca agaagacgga      60
cgacgtcgcc ggtgacggca ccacgacggc caccgtgctc gcccaggcgc tggtgcgcga     120
gggtctgcgc aatgtcgctg ccggtgccaa cccgctgagc ctgaagcgcg gtatcgagaa     180
ggcagtcgag aaggtcaccg agaccctgct caagtcggcc aaggaggtcg agaccaagga     240
```

| | |
|---|---|
| ccagatcgct gccaccgcag cgatttccgc gggggaccag tcgatcggcg acctgatcgc | 300 |
| cgaggcgatg gacaaggtcg gcaacgaggg tgtcatcacc gtcgaggagt ccaacacctt | 360 |
| cggcctgcag cttgagctca ccgagggtat gcggttcgac aagggttaca tctcgggcta | 420 |
| cttcgtcacc gacgccgagc gtcaggaagc cgtcctggaa gacccgtaca tcctgctggt | 480 |
| cagctccaag gtttcgacgg tcaaggacct gctcccgctg ctggagaagg tcattcaggc | 540 |
| cggcaagccg ctgctgatca tcgccgagga cgtcgagggc gaggcgctga gcaccctggt | 600 |
| cgtc | 604 |

<210> SEQ ID NO 23
<211> LENGTH: 604
<212> TYPE: DNA
<213> ORGANISM: Mycobacterium intracellulare

<400> SEQUENCE: 23

| | |
|---|---|
| ggaggacccg tacgagaaga tcggcgccga gctggtcaag gaagtcgcca agaagaccga | 60 |
| cgacgtcgcc ggtgacggca cgacgacggc cacggtgctg gctcaggcgt tggtccgcga | 120 |
| gggcctgcgt aacgtcgccg ccggcgccaa cccgctgggt ctcaagcgcg gcatcgagaa | 180 |
| ggccgtcgag aaggtcaccg agaccctgct caagtcggcc aaggaggtcg agaccaagga | 240 |
| ccagatcgct gccaccgcgg cgatttcggc gggcgaccag tcgatcggtg acctcatcgc | 300 |
| cgaggggatg gacaaggtcg gcaacgaggg cgtcatcacc gtcgaggagt ccaacacctt | 360 |
| cggcctgcag ctcgagctca ccgagggcat gcggttcgac aagggctaca tctcgggcta | 420 |
| cttcgtcacc gacgccgagc gtcaggaagc ggtcctcgag gaccccttca tcctgctggt | 480 |
| cagctccaag gtgtcgacgg tcaaggacct gctgccgctg ctggagaagg tcatccaggc | 540 |
| cggcaagccg ctgctgatca tcgccgagga cgtcgagggt gaggctctga gcaccctggt | 600 |
| cgtc | 604 |

<210> SEQ ID NO 24
<211> LENGTH: 604
<212> TYPE: DNA
<213> ORGANISM: Mycobaterium kansasii Type I

<400> SEQUENCE: 24

| | |
|---|---|
| ggaggacccg tacgagaaga tcggcgccga gctggtcaag gaagtcgcca agaagaccga | 60 |
| cgacgtcgct ggcgacggca ccaccacggc caccgtgctt gcgcaggcgc tggtcaaaga | 120 |
| gggcctgcgc aacgtcgcgg ccggcgccaa cccgctgggc ctcaagcgcg gcatcgagaa | 180 |
| ggccgtcgag aaggtcaccg agacgctgct caagggcgcc aaggaggtcg agaccaagga | 240 |
| gcagatcgcg gcgaccgcgg ccatctccgc cggcgaccag tcgatcggcg acctgatcgc | 300 |
| cgaggcgatg gacaaggtcg gcaacgaggg tgtcatcacc gtcgaggagt ccaacacctt | 360 |
| cggcctgcaa ctcgagctca ccgagggcat gcggttcgac aagggttaca tctccggcta | 420 |
| cttcgtcacc gacgccgagc gtcaggaagc ggttctggag gaccccctaca tcctgctggt | 480 |
| cagctcgaag gtatcgacgg tcaaggacct gctgccgctg ctggagaagg tcatccaggc | 540 |
| cggcaagccg ctgctgatca tcgccgagga cgtcgagggc gaggcgctgt ccaccctggt | 600 |
| cgtc | 604 |

<210> SEQ ID NO 25
<211> LENGTH: 604
<212> TYPE: DNA
<213> ORGANISM: Mycobaterium kansasii Type II -continued

```
<400> SEQUENCE: 25
ggaggacccg tacgagaaga tcggcgccga gctggtcaag gaagtcgcca agaagaccga 60
cgacgtcgcc ggcgacggca ccaccacggc cactgtgctc gcgcaggcgt tggtcaaaga 120
gggcctgcgc aacgtcgcgg ccggcgccaa cccactgggc ctgaagcgcg gcatcgagaa 180
ggcagtcgag aaggtcaccg agacgctgct caagggcgcc aaggaggtcg agaccaagga 240
gcagatcgct gccaccgcgg ccatctccgc gggtgaccag tcgatcggcg acctgatcgc 300
cgaggcgatg gacaaggtgg gcaacgaggg tgtcatcacc gtcgaggagt ccaacacctt 360
cggcctgcag ctcgagctca ccgagggtat gcggttcgac aagggctaca tctccggcta 420
cttcgtcacc gacgccgagc gtcaggaagc agttctggag gacccctaca tcctgctggt 480
cagctccaag gtgtccaccg tcaaggacct gctgccgctg ctggagaagg tcatccaggc 540
cggcaagccg ctgctgatca tcgccgagga cgtcgagggc gaggcgctgt ccaccctggt 600
cgtc 604

<210> SEQ ID NO 26
<211> LENGTH: 604
<212> TYPE: DNA
<213> ORGANISM: Mycobaterium kansasii Type III
<400> SEQUENCE: 26
ggaggacccg tacgagaaga tcggcgccga gctggtcaag gaagtcgcca agaagaccga 60
cgacgtcgcc ggcgacggca ccaccacggc cactgtgctc gcgcaggcgc tcgtcaagga 120
gggcctgcgc aacgtggcgg ccggcgccaa cccgctgggc ctgaagcgcg gcatcgagaa 180
ggccgtcgag aaggtcaccg agaccttgtt caagggtgcc aaggaggtcg agaccaagga 240
gcagatcgcg gccaccgcgg ccatctcggc cggtgaccag tcgattggcg acctgatcgc 300
cgaggcgatg gacaaggtag gcaacgaggg tgtcatcacc gtcgaggagt ccaacacctt 360
aggcctgcag ctcgagctca ccgagggtat gcgctttgac aagggctaca tctccggcta 420
cttcgtcacc gacgccgagc gtcaggaagc agtgctggaa gacccctaca tcctgctggt 480
cagctccaag gtgtcgacgg tcaaggacct gctgccgctg ctggagaagg tcatccaggc 540
cggcaagccg ctgctgatca tcgccgagga cgtcgagggt gaggctttga gcaccctggt 600
cgtg 604

<210> SEQ ID NO 27
<211> LENGTH: 604
<212> TYPE: DNA
<213> ORGANISM: Mycobacterium leprae
<400> SEQUENCE: 27
ggaggacccg tacgagaaga ttggcgctga gttggtcaag gaagtcgcca agaagacaga 60
tgacgtcgcc ggtgatggca ccacgacggc caccgtgctg gcccaggcat tggtcaaaga 120
gggcctacgc aacgtcgcgg ccggcgccaa cccgctaggt ctcaagcgtg gcatcgagaa 180
agctgtcgat aaggtaactg agactctgct caaggacgct aaggaggtcg aaaccaagga 240
acaaattgct gccactgcag cgatttcggc gggtgaccag tcgatcggtg atctgatcgc 300
cgaggcgatg gacaaggttg gcaacgaggg tgttatcacc gtcgaggaat ccaacacctt 360
cggtctgcag ctcgagctca ccgagggaat gcggttcgac aagggctaca tttcgggcta 420
cttcgtcacc gacgccgagc gtcaggaagc tgtcctagag gagccctaca tccttctggt 480
```

-continued

```
cagctccaaa gtgtctaccg tcaaggacct gctgccgctg ctagagaagg tcatccaggc    540
cggcaagtcg ctgctgatca ttgctgagga tgtcgagggt gaggcgttgt ctaccctggt    600
cgtc                                                                 604
```

<210> SEQ ID NO 28
<211> LENGTH: 604
<212> TYPE: DNA
<213> ORGANISM: Mycobacterium malmoense

<400> SEQUENCE: 28

```
ggaggacccg tacgagaaga tcggcgccga gctggtcaag gaagtcgcca agaagaccga     60
cgacgtggcc ggtgacggca cgacgacggc caccgtgctg gcgcaggcgc tggtcaaaga    120
gggcctgcgc aacgtcgcgg ccggtgccaa cccgctcagc ctcaagcgcg gcatcgagaa    180
ggcggtcgag aaggtcaccg agaccctgct caagtcggcc aaggaggtcg agaccaagga    240
gcagatcgcc gcgaccgccg cgatctcggc gggcgaccag tcgatcggtg acctgatcgc    300
cgaggcgatg gacaaggtcg gcaacgaggg cgtcctcacc gtcgaggagt ccaacacctt    360
cggcctgcag ctcgagctca ccgagggcat gcggttcgac aagggctaca tctcgggcta    420
cttcgtcacc gaccccgagc gtcaggaagc ggtcctggag gacccctaca tcctgctggt    480
cagctccaag gtgtcgacgg tcaaggacct gctgccgctg ctggagaagg tcattcaggc    540
cggcaagccg ctgctgatca tcgccgagga cgtcgagggc gaggcgctct ccaccctggt    600
cgtc                                                                 604
```

<210> SEQ ID NO 29
<211> LENGTH: 604
<212> TYPE: DNA
<213> ORGANISM: Mycobacterium marinum

<400> SEQUENCE: 29

```
ggaggacccg tacgagaaga tcggcgctga gctggtcaag gaagttgcca agaagaccga     60
cgacgtggcc ggtgacggca cgacgacggc caccgtgctg gcccaggcgc tggtcaagga    120
aggcctgcgc aacgttgcgg ccggtgccaa cccgctcggt ctgaagcgcg gcatcgagaa    180
ggcagtcgag aaggtcaccg agaccttgct caagtcggcc aaagaggtcg agaccaagga    240
gcagatcgcg gcgaccgcag ccatctccgc cggcgaccag tcgatcggcg acctgatcgc    300
cgaggcgatg gacaaggtgg gcaacgaggg cgtcatcacc gtcgaggagt ccaacacctt    360
cggcctgcag ctcgagctca ccgaggggat gcggttcgac aagggctaca tctcgggcta    420
cttcgtcacc gacgccgagc gtcaggaagc ggtcctggag gacccctaca tcctgctggt    480
cagttccaag gtgtccaccg tgaaggacct gctgccgctg ctggagaagg tcattcaggg    540
cggcaagccg ctgctgatca tcgccgagga cgtcgagggc gaggcgctgt ccaccctggt    600
cgtc                                                                 604
```

<210> SEQ ID NO 30
<211> LENGTH: 604
<212> TYPE: DNA
<213> ORGANISM: Mycobacterium mucogenicum

<400> SEQUENCE: 30

```
ggaggacccg tacgagaaga tcggcgctga gctggtcaag gaagttgcca agaagacgga     60
cgacgtcgct ggcgacggca ccaccaccgc caccgtgctg gcccaggccc tggttcgcga    120
aggcctgcgc aacgtcgctg ccggcgccaa cccgctcggc ctgaagcgcg gcatcgagaa    180
```

```
ggccgtcgag gctgtcacca agggcctgct ggcttccgcc aaggaggtcg agaccaagga    240
gcagatcgct gccaccgccg gatctcggcc ggtgaccag tccatcggcg acctgatcgc    300
cgaggccatg gacaaggtcg gcaacgaggg tgtcatcacc gtcgaggaga gcaacacctt    360
cggcctgcag ctggagctca ccgagggtat gcgcttcgac aagggctaca tctcggggta    420
cttcgtgacc gacgccgagc gtcaggaagc ggtcctcgag acccgttca tcctgctggt    480 cagctcgaag atctcgaccg tcaaggacct gctgccgctg ctggagaagg tcatccagtc    540
gggcaagccg ctgctgatca tcgccgagga cgtcgagggc aagccctgt cgaccctggt    600 cgtc                                                                 604
```

`<210>` SEQ ID NO 31
`<211>` LENGTH: 604
`<212>` TYPE: DNA
`<213>` ORGANISM: Mycobacterium neoaurum

`<400>` SEQUENCE: 31

```
ggaggacccg tacgagaaga tcggcgccga gctggtcaaa gaggtcgcca agaagaccga     60
tgacgtcgcg ggcgacggca ccaccaccgc caccgtgctg gcccaggccc tggttcgcga    120
aggtctgcgc aacgtcgcgg ccggcgccaa ccccctcggc ctgaagcgcg gcatcgagaa    180
ggccgtcgcg gccgtcaccg agcgcctgct ctcgaccgcc aaagaggtcg agaccaagga    240
gcagatcgct gccaccgcgg gcatctccgc cggtgaccag tcgatcggtg acctgatcgc    300
cgaggcgctg gacaaggtcg gcaacgaggg tgtcatcacc gtcgaggagt ccaacacctt    360
cggcctgcag ctggagctca ccgagggtat gcgcttcgac aagggctaca tctcggggta    420
cttcgtgacc gacgccgagc gtcaggaagc cgtcctggag gatccctaca tcctgctggt    480
cagctccaag gtctcgaccg tcaaggacct gctgccgctg ctggagaagg tcatccagtc    540
cggcaagccg ttgctgatca tcgccgagga cgtcgagggc aagccctgt cgaccctggt    600 ggtc                                                                 604
```

`<210>` SEQ ID NO 32
`<211>` LENGTH: 604
`<212>` TYPE: DNA
`<213>` ORGANISM: Mycobacterium nonchromogenicum

`<400>` SEQUENCE: 32

```
ggaggatccc tacgagaaga tcggcgctga gctggtcaaa gaggtcgcca agaagactga     60
cgacgtcgcg ggtgacggca ccaccaccgc caccgtgctc gcccaggccc tggtcaagga    120
aggcctgcgc aacgtggccg ccggcgccaa cccgctgggt ctgaagcgcg gcatcgagaa    180
ggccgttgag aaggtcacct cgaccctgct ggcttcggcc aaggaggtcg agaccaagga    240
gcagatcgcg gccaccgccg gtatctccgc gggtgaccag agcatcggtg acctgatcgc    300
cgaggccatg gacaaggtcg gcaacgaagg tgtcatcacc gtcgaggagt ccaacacctt    360
cggcctgcag ctggagctca ccgagggcat gcgcttcgac aagggctaca tctcggggta    420
cttcgtgacc gacgccgagc gtcaggaagc cgtcctggag acccctaca tcctgctggt    480 cagctcgaag atctcgaccg tcaaggacct gctgcccttg ctggagaagg tcatccagtc    540
cggcaagccg ttgctgatca tcgccgagga cgtcgagggc gaggccctgt cgaccctggt    600
cgtg                                                                 604
```

`<210>` SEQ ID NO 33

-continued

<211> LENGTH: 604
<212> TYPE: DNA
<213> ORGANISM: Mycobaterium paratuberculosis

<400> SEQUENCE: 33

```
ggaggacccg tacgagaaga tcggcgccga gctggtcaag gaagtcgcca agaagaccga     60
cgacgtcgcc ggtgacggca cgacgacggc cacggtgctc gcccaggcgt tggtccgcga    120
gggcctgcgc aacgtcgcgg ccggcgccaa cccgctgggt ctcaagcgcg gcatcgagaa    180
ggccgtcgag aaggtcaccg agaccctgct caagtcggcc aaggaggtcg agaccaagga    240
ccagatcgct gccaccgcgg ccatctccgc gggcgaccag tcgatcggcg acctgatcgc    300
cgaggcgatg gacaaggtcg gcaacgaggg cgtcatcacc gtcgaggagt ccaacacctt    360
cggcctgcag ctcgagctca ccgagggtat gcggttcgac aagggttaca tctcgggcta    420
cttcgtcacg gacgccgagc gtcaggaagc ggtcctcgag gacccgttca tcctgctggt    480
cagctccaag gtctcgaccg tcaaggacct gctgccgctg ctggagaagg tcatccaggc    540
cggcaagccg ctgctgatca tcgccgagga cgtcgagggc gaggccctgt ccaccctggt    600
cgtc                                                                 604
```

<210> SEQ ID NO 34
<211> LENGTH: 604
<212> TYPE: DNA
<213> ORGANISM: Mycobaterium phlei

<400> SEQUENCE: 34

```
cgaggatccg tacgagaaga tcggcgccga gctggtcaaa gaggtcgcca agaagaccga     60
cgatgtcgcg ggtgacggca ccaccaccgc caccgtcctg gcccaggcgc tggtgcgcga    120
gggtctgcgc aacgttgccg ccggcgccaa cccgatggct ctgaagcgcg gtatcgagaa    180
ggccgtcgag aaggtcaccg agaccctgct gaagtcggcc aaggaggtcg agaccaagga    240
gcagatcgct tcgaccgccg cgatctcggc cggcgacacc cagatcggcg agctgatcgc    300
cgaggccatg gacaaggtcg gcaacgaggg tgtcatcacc gtcgaggaga gcaacacctt    360
cggcctgcag ctggagctca ccgagggtat gcgcttcgac aagggctaca tctcgggtta    420
cttcgtgacc gacgccgagc gtcaggaagc cgtcctcgag gatccgtaca tcctgctggt    480
gtcgggcaag gtctcgaccg tcaaggacct gctgccgctg ctggagaagg tcatccagtc    540
gggcaagccg ctgctgatca tcgccgagga cgtcgagggc gaggccctgt cgaccctggt    600
cgtg                                                                 604
```

<210> SEQ ID NO 35
<211> LENGTH: 604
<212> TYPE: DNA
<213> ORGANISM: Mycobacterium peregrinum

<400> SEQUENCE: 35

```
ggaggacccg tacgagaaga tcggcgctga gctggtcaaa gaggtcgcca agaagaccga     60
cgacgtcgcg ggtgacggca ccaccaccgc caccgttctg gcccaggccc tggttcgcga    120
aggtctgcgc aacgtcgctg ccggcgccaa cccgctcggc ctgaagcgcg gcatcgagaa    180
ggctgtcgag aaggtcaccg agaccctcct gaagtccgcc aaggaggtgg agaccaagga    240
gcagatcgct gccaccgccg gtatctccgc cggagaccag tccatcggcg acctgatcgc    300
cgaggccatg gacaaggtcg gcaacgaggg tgtcatcacc gtcgaggaga gcaacacctt    360
cgggctgcag ctggagctca ccgagggcat gcgcttcgac aagggctaca tctcgggcta    420
```

```
cttcgtgacc gacgccgagc gtcaggaagc cgtcctggag gatccctaca tcctgctggt    480
cagctcgaag atctcgaccg tcaaggacct gctgccgctg ctggagaagg tcatccagtc    540
cggcaagccg ctgctgatca tcgccgagga cgtcgagggc gaagccctgt cgaccctggt    600
ggtc                                                                  604

<210> SEQ ID NO 36
<211> LENGTH: 604
<212> TYPE: DNA
<213> ORGANISM: Mycobacterium scrofulaceum

<400> SEQUENCE: 36
ggaggacccg tacgagaaga tcggcgccga gctggtcaag gaagtcgcca agaagaccga     60
cgacgtcgcc ggtgacggca cgacgacggc cacggtgctg gcccaggcgc tggtcaagga    120
gggcctgcgc aacgtcgcgg cgggcgccaa cccgctgagc ctcaagcgcg gcatcgagaa    180
ggcggtcgag aaggtcaccg agaccctgct caagtcggcc aaggaggtcg agaccaagga    240
ccagatcgcc gccaccgcgg cgatttcggc gggcgaccag tcgatcggcg acctgatcgc    300
cgaggcgatg gacaaggtcg gcaacgaggg cgtcatcacc gtcgaggagt ccaacacctt    360
cggcctgcag ctcgagctca ccgagggcat gcggttcgac aagggctaca tctcgggcta    420
cttcgtcacc gacgccgagc ggcaggaagc ggtcctggag gaccctaca tcctgctggt    480 cagctcgaag gtgtcgacgg tcaaggacct gctgccgctg ttggagaagg tcatccaggc    540
cggcaagccg ctgctgatca tcgccgagga cgtcgagggc gaggcgcttt ccaccctggt    600
cgtc                                                                  604

<210> SEQ ID NO 37
<211> LENGTH: 604
<212> TYPE: DNA
<213> ORGANISM: Mycobacterium senegalense

<400> SEQUENCE: 37
ggaggacccg tacgagaaga tcggcgctga gctggtcaag gaagtcgcca agaagactga     60
cgacgtcgcg ggtgacggca ccaccaccgc caccgttctg gcccaggccc tggttcgtga    120
aggtctgcgt aacgtcgctg ccggcgccaa cccgctcggc ctgaagcgcg gcatcgagaa    180
ggccgtcgag aaggtcaccg agacgctgct caagagcgcc aaggaggtgg agaccaagga    240
gcagatcgct gccaccgccg cgatctcggc gggcgacacc cagatcggca agctgatcgc    300
cgaggccatg gacaaggtcg gcaacgaggg tgtcatcacc gttgaggagt ccaacacctt    360
cgggctgcag ctcgagctca ccgagggtat gcgcttcgac aagggctaca tctcgggtta    420
cttcgtgacc gacgccgagc gtcaggaagc ggtcctcgag gatccctgca tcctgctcgt    480
gtcgtccaag gtgtcgaccg tcaaggatct gctcccgttg ctggagaagg tcattcaggc    540
cggcaagccg gtgctgatca tcgccgagga cgtcgagggt gaggccctgt cgaccctggt    600
ggtc                                                                  604

<210> SEQ ID NO 38
<211> LENGTH: 604
<212> TYPE: DNA
<213> ORGANISM: Mycobacterium shimoidei

<400> SEQUENCE: 38
ggaggacccg tacgagaaga tcggcgccga gctggtcaag gaagtcgcca agaagaccga     60
```

```
cgacgtcgcc ggtgacggca ccaccaccgc caccgtgctg gcccaggcgc tggtccacga    120
ggggctgcgc aacgtcgcgg ccggtgccaa cccgctcagc ctgaaacgcg gtatcgagaa    180
ggccgttgag aaggtcaccg agaccttgct caagggcgcc aaggaagtcg agaccaagga    240
gcagatcgcg gccacggcgg ccatctccgc cggtgaccag tcgatcggcg acctgatcgc    300
cgaggcgatg gacaaggtcg gcaacgaggg cgtcatcacc gtcgaggagt ccaacacctt    360
cggcctgcag ctcgagctca ccgagggtat gcggttcgac aagggctaca tttcgggtta    420
cttcgtcacc gacgccgagc gtcaggaggc tgtgctcgag agccctaca tcctgctggt    480 cagctccaag gtgtcgacgg tcaaggacct gctgccgctg ctggagaagg tcatgcaggc    540
cggcaagccg ctgctgatca tcgccgagga cgtcgagggc gaggctttga gcaccctggt    600
cgtc                                                                  604

<210> SEQ ID NO 39
<211> LENGTH: 604
<212> TYPE: DNA
<213> ORGANISM: Mycobacterium simiae

<400> SEQUENCE: 39
ggaggacccc tacgagaaga tcggcgctga gctggtcaag gaagtcgcca agaagaccga     60
cgacgtcgcc ggtgacggca ccacgacggc caccgtgctc gctcaggcgc tcgtcaagga    120
gggcctgcgc aacgtggcgg ccggcgccaa cccgctgggc ctcaagcgcg gcatcgagaa    180
ggccgtcgaa aaggtcaccg agacgctgct gaagtcggcc aaggatgtcg agaccaagga    240
ccagatcgct gccaccgccg cgatttccgc gggcgaccag tcgatcggcg acctgatcgc    300
cgaggcgatg gacaaggtcg gcaacgaggg cgtcatcacc gtcgaggagt ccaacacctt    360
cgggctgcag ctcgagctca ccgagggtat gcgcttcgac aagggctaca tctcgggcta    420
cttcgtcacc gacgccgagc gtcaggaagc cgtcctggag gacccgttca tcctgctggt    480
cagctccaag gtgtcgacgg tcaaggacct gctgccgctg ctggagaagg tcatccaggc    540
cggcaagccg ctgctgatca tcgccgagga cgtcgagggc gaggcgctga gcaccctggt    600
cgtc                                                                  604

<210> SEQ ID NO 40
<211> LENGTH: 604
<212> TYPE: DNA
<213> ORGANISM: Mycobacterium smegmatis

<400> SEQUENCE: 40
cgaggacccc tacgagaaga tcggtgctga gctcgtcaaa gaggtcgcca agaagaccga     60
cgatgtcgct ggcgacggca ccaccaccgc caccgtcctg gctcaggccc tggttcgcga    120
aggcctgcgc aacgtcgctg ccggcgccaa cccgctcggc ctgaagcgcg gcatcgagaa    180
ggccgtcgag aaggtcaccg agaccctgct gaagtccgcc aaggaggtgg agaccaagga    240
gcagatcgct gccaccgccg gtatctccgc cggtgaccag tccatcggcg acctgatcgc    300
cgaggccatg gacaaggtcg gcaacgaggg tgtcatcacc gtcgaggagt ccaacacctt    360
cggcctgcag ctcgagctca ccgagggtat gcgcttcgac aagggctaca tctcgggtta    420
cttcgtgacc gacgccgagc gtcaggaagc ggtcctcgag gatccctaca tcctgctggt    480
cagctcgaag gtctcgaccg tcaaggacct gctgccgctg ctggagaagg tcatccagtc    540
cggcaagccg ctgctgatca tcgccgagga cgtcgagggc gaagcccgtg cgaccctggt    600
ggtc                                                                  604
```

<210> SEQ ID NO 41
<211> LENGTH: 604
<212> TYPE: DNA
<213> ORGANISM: Mycobacterium szulgai

<400> SEQUENCE: 41

```
ggaggacccg tacgagaaga tcggcgccga gctggtcaag gaagttgcca agaagaccga    60
cgacgtcgcc ggtgacggca cgacgacggc caccgtgttg cccaggcgcg tggtcaagga   120
gggcctgcgc aacgtagcgg ccggcgccaa cccgctgggt ctcaagcgcg gcatcgagaa   180
ggccgtcgag aagatcaccg agaccctgct caagtcggct aaggacgtcg agaccaagga   240
gcagatcgcg gccaccgcgg ccatctccgc gggcgaccag tcgatcggcg acttgatcgc   300
cgaggcgatg gacaaggtcg gcaatgaggg cgtcatcacc gtcgaggagt ccaacaccct   360
cggcctgcag ctcgagctca ccgagggcat gcggttcgac aagggctaca tctcgggcta   420
cttcgtcacc gacgccgagc gtcaggaggc cgtcctcgag gacccttaca tcctgttggt   480
cgcctccaag gtgtcgacgg tcaaggacct gttgccgctg ctggagaagg tcatccaggg   540
cggcaagccg ctgctgatca tcgccgagga cgtcgagggc gaggctttga gcaccctggt   600
cgtc                                                                604
```

<210> SEQ ID NO 42
<211> LENGTH: 604
<212> TYPE: DNA
<213> ORGANISM: Mycobacterium terrae

<400> SEQUENCE: 42

```
ggaggacccc tacgagaaga tcggcgccga gctggtcaaa gaggtcgcca agaagaccga    60
cgatgtcgcc ggtgacggca ccaccacggc caccgtgctg gcacaggcgc tggtcaagga   120
aggcctgcgc aacgtggccg ccggcgccaa cccgctggcc ctgaagcgcg gcatcgagaa   180
ggccgtcgag aaggtctccg agaccctgct gaaggacgcc aaggaggtcg agaccaagga   240
gcagatcgcg gctaccgccg gaatctccgc gggcgaccag tccatcggtg acctgatcgc   300
cgaggcgatg gacaaggtcg gcaacgaggg tgtcatcacc gtcgaggagt ccaacaccct   360
cggcctgcag ctggagctca ccgagggtat gcgcttcgac aagggctaca tctcgggtta   420
cttcgtcacc gacgccgacc gtcaggaagc ggttctcgag gacccctaca tcctgctggt   480
cagctccaag atctcgacgg tcaaggacct gctcccactg ctggagaagg tcattcaggg   540
cggtaagccg ctgctgatca tcgccgagga cgtcgagggc gaggccctgt ccaccctggt   600
ggtc                                                                604
```

<210> SEQ ID NO 43
<211> LENGTH: 604
<212> TYPE: DNA
<213> ORGANISM: Mycobacterium thermoresistibile

<400> SEQUENCE: 43

```
ggaggacccc tacgagaaga tcggcgctga gctggtcaag gaagtcgcca agaagaccga    60
cgacgtcgcc ggcgacggca ccaccaccgc caccgtcctg gctcaggcgc tggtgaagga   120
aggtttgcgc aacgtcgcgg ccggggccaa cccgctcgct ctgaagcgcg gcatcggagc   180
cgctgtcgag aaggtcaccg agaccctgct caagtcggcc aaggaggtcg agaccaagga   240
gcagatcgcc aacaccgccg cgatctcggc cggcgaccag cagaccggtg agctgatcgc   300
```

```
cgaggcgatg acaaggtcg gcaacgaggg tgtcatcacc gtcgaggagt cgcagaccttt    360 cggtctgcag ctcgagctca ccgagggtat gcgcttcgac aagggctaca tctcggggta    420
cttcgtgacc gacgcggagc ggcaggaagc cgttctggag gatccctaca tcctgctggt    480
cagctcgaag gtctcgactg tcaaggatct gctgccgctg ctggagaagg tcatccagtc    540
cggcaggccg ctgctgatca tcgccgagga cgtcgaaggc gaggcgctgt cgaccctggt    600
cgtc                                                                 604

<210> SEQ ID NO 44
<211> LENGTH: 604
<212> TYPE: DNA
<213> ORGANISM: Mycobacterium triviale

<400> SEQUENCE: 44
ggaggacccg tacgagaaga tcggcgccga gctggtcaag gaagtcgcca agaagaccga     60
cgatgtcgcc ggtgacggca ccaccacggc caccgtgctc gcccaggcgc tggtgcgcga    120
gggcctgcgc aacgtcgccg cgggcgccaa cccgatgggc ctgaagcgcg gcatcgaggc    180
ggccaccgag aagatcgccg agaccctgct caagggcgcc aaagaggtgg agaccaagga    240
gcagatcgct gccaccgccg ggatctccgc cggggacagc tccatcggtg agctgatcgc    300
cgaggcgatg gacaaggtcg gcaacgaggg tgtcatcacc gtcgaggagg cccagacctt    360
cggcctgcag ctcgagctca ccgagggtat gcgcttcgac aagggctaca tctccggcta    420
cttcgtcacc gacgccgagc gtcaggaggc cgtgctggag gaccctaca tcctgctggt     480 gtccggcaag gtgtccaccg tcaaggacct gcttccgctg ctggagaagg tcatccagtc    540
cggcaagccg ctgctgatca tcgccgagga cgtcgagggc gaggcgctgt cgaccctggt    600
ggtc                                                                 604

<210> SEQ ID NO 45
<211> LENGTH: 604
<212> TYPE: DNA
<213> ORGANISM: Mycobacterium tuberculosis

<400> SEQUENCE: 45
ggaggatccg tacgagaaga tcggcgccga gctggtcaaa gaggtagcca agaagaccga     60
tgacgtcgcc ggtgacggca ccacgacggc caccgtgctg gcccaggcgt tggttcgcga    120
gggcctgcgc aacgtcgcgg ccggcgccaa cccgctcggt ctcaaacgcg gcatcgaaaa    180
ggccgtggag aaggtcaccg agaccctgct caagggcgcc aaggaggtcg agaccaagga    240
gcagattgcg gccaccgcag cgatttcggc gggtgaccag tccatcggtg acctgatcgc    300
cgaggcgatg gacaaggtgg gcaacgaggg cgtcatcacc gtcgaggagt ccaacaccttt   360 tgggctgcag ctcgagctca ccgagggtat gcggttcgac aagggctaca tctcggggta    420
cttcgtgacc gaccccggagc gtcaggaggc ggtcctggag gaccccctaca tcctgctggt  480 cagctccaag gtgtccactg tcaaggatct gctgccgctg ctcgagaagg tcatcggagc    540
cggtaagccg ctgctgatca tcgccgagga cgtcgagggc gaggcgctgt ccaccctggt    600
cgtc                                                                 604

<210> SEQ ID NO 46
<211> LENGTH: 604
<212> TYPE: DNA
<213> ORGANISM: Mycobacterium ulcerans

<400> SEQUENCE: 46
```

```
ggaggacccg tacgagaaga ttggcgctga gctggtcaag gaagttgcca agaagaccga    60
cgacgtggcc ggtgacggca cgacgacggc caccgtgctg gcccaggcgc tggtcaagga   120
aggcctgcgc aacgttgcgg ccggtgccaa cccgctcggt ctgaagcgcg gcatcgagaa   180
ggcagtcgag aaggtcaccg agaccctgct caaatcggcc aaagaggtcg agaccaagga   240
gcagatcgcg gcgaccgcag ccatctccgc cggcgaccag tcgatcggcg acctgatcgc   300
cgaggcgatg gacaaggtgg gcaacgaggg cgtcatcacc gtcgaggagt ccaacacctt   360
cggcctgcag ctcgagctca ccgaggggat gcggttcgac aagggctaca tctcgggcta   420
cttcgtcacc gacgccgagc gtcaggaagc ggtcctggag acccctaca tcctgctggt    480 cagctccaag gtgtccaccg tcaaggacct gctgccgctg ctggagaagg tcattcaggg   540
cggcaagccg ctgctgatca tcgccgagga cgtcgagggc gaggcgctgt ccaccctggt   600
cgtc                                                                604

<210> SEQ ID NO 47
<211> LENGTH: 604
<212> TYPE: DNA
<213> ORGANISM: Mycobacterium vaccae

<400> SEQUENCE: 47
ggaggacccg tacgagaaga tcggcgctga gctggtcaaa gaggtcgcca agaagaccga    60
cgacgtcgcg ggcgacggta ccaccaccgc caccgtgctc gctcaggctc tggttcgcga   120
aggcctgcgc aacgtcgcag ccggcgccaa cccgctcggc ctcaagcgtg gcatcgagaa   180
ggctgtcgag gctgtcaccc agtcgctgct gaagtcggcc aaggaggtcg agaccaagga   240
gcagatttct gccaccgcgg cgatctccgc cggcgacacc cagatcggcg agctcatcgc   300
cgaggccatg gacaaggtcg gcaacgaggg tgtcatcacc gtcgaggagt cgaacacctt   360
cggcctgcag ctcgagctca ccgagggtat gcgcttcgac aagggctaca tctcgggtta   420
cttcgtgacc gacgccgagc gccaggaagc cgtcctggag gatccctaca tcctgctggt   480
cagctccaag gtgtcgaccg tcaaggatct gctcccgctg ctggagaagg tcatccaggc   540
cggcaagccg ctgctgatca tcgccgagga cgtcgagggc gaggccctgt ccacgctggt   600
ggtc                                                                604

<210> SEQ ID NO 48
<211> LENGTH: 604
<212> TYPE: DNA
<213> ORGANISM: Mycobacterium wolinskyi

<400> SEQUENCE: 48
ggaggacccg tacgagaaga tcggcgctga gctggtcaaa gaggtcgcca agaagaccga    60
cgacgtcgcc ggcgacggca ccaccaccgc caccgttttg cccaggctc tggttcgcga    120 aggtctgcgc aacgtcgcgg ccggcgccaa cccgctcggc ctgaagcgcg gcatcgagaa   180
ggccgtcgag aaggtcaccg agacgctgct gaagagcgcc aaggaggtgg agaccaagga   240
gcagatcgct gccaccgccg gtatctccgc cggtgaccag tccatcggcg acctgatcgc   300
cgaggccatg gacaaggtcg gcaacgaggg tgtcatcacc gtcgaggaga gcaacacctt   360
cggcctgcag ctggagctca ccgagggtat gcgcttcgac aagggctaca tctcgggtta   420
cttcgtgacc gacgccgagc gtcaggaagc cgtcctcgag gatccctaca tcctgctggt   480
cagctcgaag gcctcgaccg tcaaggacct gctgccgctg ctggagaagg tcatccagtc   540
```

```
cggcaagccg ctgctgatca tcgccgagga cgtcgagggc gaggccctgt cgaccctggt    600
ggtc                                                                 604

<210> SEQ ID NO 49
<211> LENGTH: 604
<212> TYPE: DNA
<213> ORGANISM: Mycobacterium parafortuitum

<400> SEQUENCE: 49
ggaggacccg tacgagaaga tcggcgctga gctggtcaaa gaggtcgcca agaagaccga     60
cgacgtcgcg ggcgacggca ccaccaccgc caccgtgctc gctcaggccc tggttcgcga    120
aggtctgcgc aacgtcgcag ccggcgccaa cccgctcggc ctcaagcgtg gcatcgagaa    180
ggctgtcgag gctgtcaccc agggtctgct gaagtcggcc aaggaggtcg agaccaagga    240
gcagatcgct gccaccgccg cgatctccgc cggcgacacc cagatcggcg agctcatcgc    300
cgaggccatg gacaaggtcg gcaacgaggg tgtcatcacc gtcgaggagt cgaacacctt    360
cggcctgcag ctggagctca ccgaaggcat gcgcttcgac aagggctaca tctcgggtta    420
cttcgtgacc gacgccgagc gtcaggaagc cgtcctggag gatccctaca ttctgctggt    480
cagctccaag atctcgacgg tcaaggacct gctgccgctg ctggagaagg tcatccagtc    540
cggcaagccg ctgctgatca tcgccgagga cgtcgagggc gaagccctgt cgaccctggt    600
ggtc                                                                 604

<210> SEQ ID NO 50
<211> LENGTH: 604
<212> TYPE: DNA
<213> ORGANISM: Mycobacterium farcinogenes

<400> SEQUENCE: 50
ggaggacccg tacgagaaga tcggcgctga gctcgtcaaa gaggtcgcca agaagaccga     60
cgacgtcgcg ggcgacggca ccaccaccgc caccgttctg gcccaggccc tggttcgcga    120
aggtctgcgc aacgtcgctg ccggcgccaa cccgctcggc ctgaagcgcg gcatcgagaa    180
ggccgtcgag aaggtcaccg agacgctgct caagagcgcc aaggaggtgg agaccaagga    240
gcagatcgct gccaccgccg gtatctccgc cggtgaccag tccatcggtg acctgatcgc    300
cgaggccatg gacaaggtcg gcaacgaggg tgtcatcacc gtcgaggaga gcaacacctt    360
cggcctgcag ctggagctca ccgagggtat gcgcttcgac aagggctaca tctcgggtta    420
cttcgtgacc gacgccgagc gtcaggaagc cgtcctggag gatccctaca tcctgctggt    480
cagctccaag gtctcgaccg tcaaggatct gctgccgctg ctggagaagg tcatccagtc    540
cggcaagccg ctgctgatca tcgccgagga cgtcgagggc gaagccctgt ccaccctggt    600
ggtc                                                                 604

<210> SEQ ID NO 51
<211> LENGTH: 604
<212> TYPE: DNA
<213> ORGANISM: Tsukamurella paurometabola

<400> SEQUENCE: 51
cgaggatccc tacgagaaga tcggcgccga gctcgtcaag gaggtcgcca agaagaccga     60
cgacgtcgcg ggcgacggca ccaccaccgc caccgttctg gcccaggcgc tcgtgcgcga    120
gggtctgcgc aacgtggctg cgggtgcgaa cccgctgggc ctcaagcggg gcatcgagaa    180
ggccgtcgag gccgtgaccg agcacctgct caaggaggcc aaggaggtcg agaccaagga    240
```

```
gcagatcgct gctaccgcgg gcatctcggc cggcgacccc gccatcggtg agctcatcgc    300
cgaggccatg gacaaggtcg gcaaggaagg cgtcatcacc gtcgaggaga gcaacacctt    360
cggtctccag ctggagctca ccgagggcat gcgcttcgac aagggcttca tctccggcta    420
cttcgccacc gacgccgagc gtcaggaggc cgtgctcgag gacgcctaca tcctgctcgt    480
gtcgagcaag atctcgaccg tgaaggacct gctgccgctg ctggagaagg tcatccagtc    540
gggcaagccg ctcgcgatca tcgccgagga cgtcgagggc gaggccctgt cgacgctcat    600
cgtc                                                                 604

<210> SEQ ID NO 52
<211> LENGTH: 604
<212> TYPE: DNA
<213> ORGANISM: Tsukamurella tyrosinosolvens

<400> SEQUENCE: 52
cgaggatccc tacgagaaga tcggcgccga gctcgtcaag gaggtcgcca agaagaccga     60
cgacgtcgcg ggcgacggca ccaccaccgc caccgttctg gcccaggcgc tcgtgcgcga    120
gggcctgcgc aacgtggccg cgggcgcgaa cccgctgggc ctcaagcggg gcatcgagaa    180
ggccgtcgag gccgtctccg agcacctgct gaaggccgcc aaggaggtcg agaccaagga    240
gcagatcgct gctaccgcgg gcatctcggc cggcgacccc gccatcggtg agctcatcgc    300
cgaggccatg gacaaggtcg gcaaggaagg cgtcatcacc gtcgaggaga gcaacacctt    360
cggcctccag ctggagctca ccgagggcat gcgcttcgac aagggcttca tctcgggcta    420
cttcgccacc gacgccgagc gtcaggaggc cgtgctcgag gacgcctacg tgctgctcgt    480
cgccggcaag atctcgaccg tcaaggacct gctgccgctg ctggagaagg tcatccagtc    540
gggcaagccg ctcgcgatca tcgccgagga cgtcgagggc gaggccctgt cgacgctcat    600
cgtc                                                                 604

<210> SEQ ID NO 53
<211> LENGTH: 604
<212> TYPE: DNA
<213> ORGANISM: Tsukamurella pulmonis

<400> SEQUENCE: 53
cgaggatccc tacgagaaga tcggcgccga gctcgtcaag gaggtcgcca agaagaccga     60
cgacgtcgcg ggcgacggca ccaccaccgc caccgttctg gcccaggcgc tcgtgcgcga    120
gggtctgcgg aacgtggccg cgggcgcgaa cccgctgggc ctcaagcggg gcatcgagaa    180
ggcggtcgac gccgtcaccg agcacctgct gaaggccgcc aaggaggtcg agaccaagga    240
gcagatcgct gctaccgcgg gcatctcggc cggcgacccc gccatcggtg agctcatcgc    300
cgaggccatg gacaaggtcg gcgaggaagg cgtcatcacc gtcgaggaga gcaacacctt    360
cggtctccag ctggagctga ccgagggcat gcgcttcgac aagggcttca tctcgggcta    420
cttcgccacc gacgcggagc gccaggaggc cgtcctcgag gacgcctacg tgctgctcgt    480
ctcgggcaag atctcgaccg tcaaggacct gctgccgctg ctggagaagg tcatccagtc    540
gggcaagccg ctcgcgatca tcgccgagga cgtcgagggc gaggccctgt cgacgctcat    600
cgtc                                                                 604

<210> SEQ ID NO 54
<211> LENGTH: 604
<212> TYPE: DNA
```

-continued

```
<213> ORGANISM: Nocardia carnea

<400> SEQUENCE: 54
cgaggatccc tacgagaaga tcggcgccga gctggtcaag gaagtcgcca agaagaccga    60
cgacgtcgcg ggcgacggca ccaccaccgc caccgtgctc gcccaggcgc tggtgcgcga   120
gggtctgcgc aacgtggccg cgggcgcgaa cccgctgggc ctcaagcgca gcatcgagaa   180
ggccgtcgag gccgtgaccg ccaagctgct cgacaccgcc aaggaggtcg agaccaagga   240
gcagatcgcc gccaccgcgg gcatctccgc gggcgacgcg tccatcggtg agctgatcgc   300
cgaggccatg gacaaggtcg gcaaggaagg cgtcatcacc gtcgaggaga gcaacacctt   360
cggcctccag ctggagctga ccgagggcat gcgcttcgac aagggctaca tctccggcta   420
cttcgtgacc gatcccgagc gtcaggaagc ggtcctcgag gatccctaca tcctgctcgt   480
cggctcgaag gtctccaccg tcaaggacct gctgccgctg ctggagaagg tcatccaggc   540
cggcaagccg ctgctgatca tcgccgagga cgtcgagggc gaggccctgt cgaccctggt   600
cgtg                                                                604

<210> SEQ ID NO 55
<211> LENGTH: 20
<212> TYPE: DNA
<213> ORGANISM: Artificial Sequence
<220> FEATURE:
<223> OTHER INFORMATION: HSPF3

<400> SEQUENCE: 55
atcgccaagg agatcgagct                                                20

<210> SEQ ID NO 56
<211> LENGTH: 20
<212> TYPE: DNA
<213> ORGANISM: Artificial Sequence
<220> FEATURE:
<223> OTHER INFORMATION: HSPR3

<400> SEQUENCE: 56
aaggtgccgc ggatcttgtt                                                20
```